United States Patent [19]
Igarashi et al.

[11] Patent Number: 5,260,288
[45] Date of Patent: Nov. 9, 1993

[54] METHOD FOR INHIBITION OF CELL MOTILITY BY SPHINGOSINE-1-PHOSPHATE AND DERIVATIVES

[75] Inventors: Yasuyuki Igarashi; Fugiang Ruan; Yoshito Sadahira; Shigeyuki Kawa; Sen-itiroh Hakomori, all of Seattle, Wash.

[73] Assignee: The Biomembrane Institute, Seattle, Wash.

[21] Appl. No.: 863,179

[22] Filed: Apr. 3, 1992

[51] Int. Cl.$^5$ ............................................. A61K 31/66
[52] U.S. Cl. ..................................... 514/114; 514/119
[58] Field of Search ............................... 514/114, 119

Primary Examiner—Mary C. Lee
Assistant Examiner—Michael Ambrose
Attorney, Agent, or Firm—Sughrue, Mion, Zinn, Macpeak & Seas

[57] ABSTRACT

A method of inhibiting tumor cell chemotactic and/or chemoinvasion motility comprising contacting the tumor cell with an inhibitory amount of an agent selected from the group consisting of sphingosine-1-phosphate, derivatives of sphingosine-1-phosphate and mimetics of the sphingosine-1-phosphate or of the derivatives. A method of inhibiting phagokinetic activity of tumor cells and neutrophils comprising contacting the cells with a phagokinetic inhibitory amount of an agent selected from the group consisting of sphingosine-1-phosphate, derivatives of sphingosine-1-phosphate, and mimetics of the sphingosine-1-phosphate or of the derivatives. A method of inhibiting tumor cell metastasis comprising administering to a host in need of treatment a metastasis inhibitory amount of an agent selected from the group consisting of sphingosine-1-phosphate, derivatives of sphingosine-1-phosphate, and mimetics of the sphingosine-1-phosphate or of the derivatives, and pharmaceutically acceptable salts of the agent. A method of inhibiting inflammation due to motility and invasion into blood vessel walls of neutrophils comprising administering to a host in need of treatment an inflammation inhibitory amount of an agent selected from the group consisting of sphingosine-1-phosphate, derivatives of sphingosine-1-phosphate, and mimetics of the sphingosine-1-phosphate or of the derivatives, and pharmaceutically acceptable salts of the agent. A method of preparing sphingosine-1-phosphate and its derivatives.

12 Claims, 22 Drawing Sheets

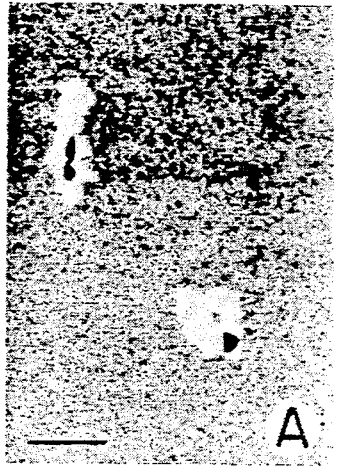 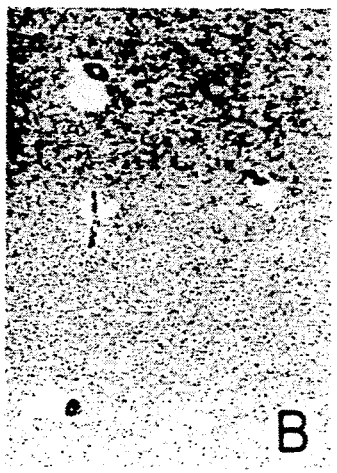 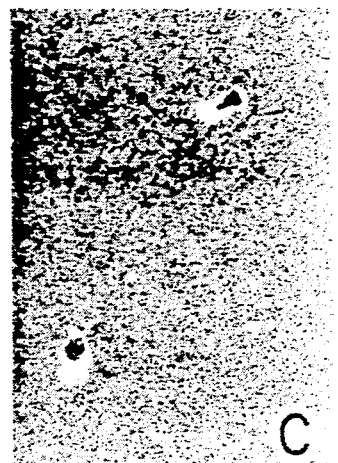
FIG. 11A  FIG. 11B  FIG. 11C
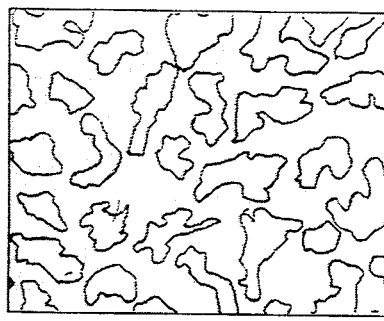 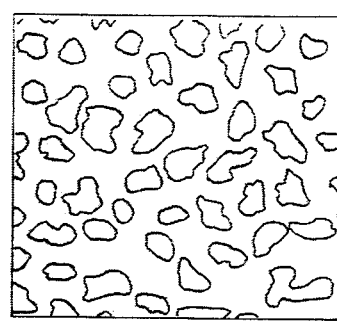 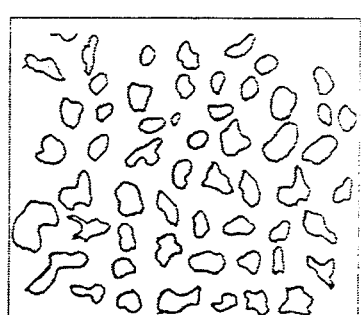
FIG. 11D  FIG. 11E  FIG. 11F

METHOD FOR INHIBITION OF CELL MOTILITY BY SPHINGOSINE-1-PHOSPHATE AND DERIVATIVES

FIELD OF THE INVENTION

The invention relates to compounds with profound effects on mammalian cell motility, methods of using the compounds and methods of chemically synthesizing the compounds.

BACKGROUND OF THE INVENTION

Sphingenine- and sphingosine-1-phosphate, collectively called sphingosine-1-phosphate (SPN-1-P), have been known for many years as products of sphingosine (SPN) kinase {Stoffel W., Hoppe-Seyler's Z. Physiol. Chem., 354: 562, 1973; 354:1311 (1973); Stoffel W., et al, ibid, 355:61 (1974); 354:169 (1973); Louie D. D., et al, J. Biol. Chem., 251:4557 (1976)}. The reaction catalyzed by sphingosine (SPN) kinase is regarded as an initial step of sphingoid base degradation to yield ethanolamine-1-phosphate and a long-chain aldehyde (e.g., palmital) by a pyridoxa phosphate-dependent lyase reaction (see FIG. 1). While SPN-1-P has been recognized as an initial catabolic product of SPN, the real physiological function of this compound has been unknown. SPN-dependent stimulation of mouse 3T3 cell growth has been shown to be independent of the protein kinase C (PKC) pathway (Zhang et al, J. Biol. Chem., 265:76 (1990)), and has been attributed to formation of SPN-1-P {Zhang et al, J. Cell Biol., 114:155 (1991)}. SPN-1-P may enhance cytoplasmic $Ca^{2+}$ release in analogy to the effect of inositol-1,4,5-triphosphate on $Ca^{2+}$ movement {Ghosh et al, Science, 248:1653 (1990)}. Although SPN-1-P was assumed in these earlier studies to induce a cell-proliferative effect of 3T3 cells, particularly in the presence of epidermal growth factor and insulin {Zhang et al (1991)}, the physiological functional role of SPN-1-P in cells has been unknown.

On the other hand, SPN-1-P is difficult to synthesize from chemical reactions. B. Weiss {J. Am. Chem. Soc., 79:5553 (1957)} was able to synthesize dihydrosphingosine-1-P (sphinganine-1-P) but not sphingenine-1-P. This effort to chemically synthesize SPN-1-P was unsuccessful, probably because of the presence of multifunctional groups in SPN. The only reported method for preparation of SPN-1-P (mainly D-erythro isomer, but containing a small amount of L-threo isomer) is by treatment of sphingosylphosphocholine with phospholipase D, isolated from Streptomuces chromofuscus {van Veldhoven P. P., Fogelsong R. J., Bell R. M., J. Lipid Res., 30:611 (1989)}.

SUMMARY OF THE INVENTION

The present inventors have found the SPN-1-P and its derivatives affect cell motility. Cell motility is an important parameter defining various pathological processes such as inflammation, tumor invasion, and metastasis.

Accordingly, one object of the invention is to provide a compound and its derivatives for inhibiting metastatic properties of malignant tumor cells, for controlling cell motility and for treating various disorders characterized by abnormal cell proliferation.

Another object of the invention is to provide a compound and its derivatives for inhibiting inflammation due to motility of neutrophils.

A further object of the invention is to provide methods of preparing a compound and its derivatives which inhibit metastatic properties of malignant tumor cells and inflammation due to motility of neutrophils.

These and other objects have been achieved by providing a method of inhibiting tumor cell chemotactic motility comprising contacting the tumor cells with an inhibitory amount of an agent selected from the group consisting of sphingosine-1-phosphate, derivatives of sphingosine-1-phosphate and mimetics of the sphingosine-1-phosphate or the derivatives.

The present invention also provides a method of inhibiting tumor cell chemoinvasion comprising contacting the tumor cells with an inhibitory amount of an agent selected from the group consisting of sphingosine-1-phosphate, derivatives of sphingosine-1-phosphate, and mimetics of the sphingosine-1-phosphate or the derivatives.

The present invention also provides a method of inhibiting phagokinetic activity of tumor cells and neutrophils comprising contacting the cells with a phagokinetic inhibitory amount of an agent selected from the group consisting of sphingosine-1-phosphate, derivatives of sphingosine-1-phosphate, and mimetics of the sphingosine-1-phosphate or the derivatives.

The present invention additionally provides a method of inhibiting tumor cell metastasis comprising administering to a host in need of treatment a metastasis inhibitory amount of an agent selected from the group consisting of sphingosine-1-phosphate, derivatives of sphingosine-1-phosphate, and mimetics of the sphingosine-1-phosphate or the derivatives, and pharmaceutically acceptable salts of the agent.

The present invention even further provides a method of inhibiting inflammation due to motility and invasion into blood vessel walls of neutrophils comprising administering to a host in need of treatment an inflammation inhibitory amount of an agent selected from the group consisting of sphingosine-1-phosphate, derivatives of sphingosine-1-phosphate and mimetics of the sphingosine-1-phosphate or the derivatives, and pharmaceutically acceptable salts of the agent.

Finally, the present invention provides sphingosine-1-phosphate and its derivatives essentially free of L-threo isomer as detected by NMR spectroscopy and a method for preparing this sphingosine-1-phosphate and its derivatives.

BRIEF DESCRIPTION OF THE FIGURES

FIGS. 11A-F depict gold sol clearance patterns of B16/F1 cells for the phagokinetic assay. FIGS. 11D-F show areas cleared in the absence of or in the presence of various concentrations of SPN-1-P.

FIG. 11A: control cells in CM without SPN-1-P;
FIG. 11B: CM plus 1.0 μM SPN-1-P;
FIG. 11C: CM plus 0.1 μM SPN-1-P;
FIG. 11D: 0 μM SPN-1-P;
FIG. 11E: 0.1 μM SPN-1-P;
FIG. 11F: 1.0 μM SPN-1-P.

FIG. 13A: thin-layer chromatography (TLC) of lipids separated from Folch's lower phase;
FIG. 13B: TLC of lipids separated from Folch's upper phase followed by incubation with $^{14}$C-TMS and extraction;
FIG. 13C: TLC of lipids separated from Folch's upper phase.

Lane 1, 0 minute. Lane 2, 10 minutes. Lane 3, 30 minutes. Lane 4, 1 hour. Lane 5, 2 hours. Lane 6, 4 hours. Lane 7, 20 hours. CER represents ceramide; CMH represents ceramide monohexoside; PE represents phosphatidyl-ethanolamine; SM represents sphingomyelin; TMS represents N,N,N-trimethylsphingosine; SPN represents sphingosine; SPN-1-P represents sphingosine-1-phosphate; and ORG represents the origin.

DETAILED DESCRIPTION OF THE INVENTION

Herein, the present inventors provide a clear demonstration that SPN-1-P inhibits cell motility of neutrophils and tumor cells, as determined by a phagokinetic track assay (on gold sol particle-coated solid phase) and an invasion assay (through a transwell chamber coated with an extracellular matrix). This inhibitory effect on SPN-1-P is shown to be much stronger than that for SPN, N,N-dimethylsphingosine (DMS), or N,N,N-trimethylsphingosine (TMS). Further, in striking contrast to DMS and TMS, SPN-1-P does not inhibit PKC. Therefore, the effect of SPN-1-P on cell motility is independent of the PKC signaling pathway.

The present inventors have also determined how to make SPN-1-P and its derivatives by chemical synthesis.

Thus, this invention deals with the chemical synthesis and use of SPN-1-P, its derivatives, or mimetics as inhibitors of cell motility in general, and their use in suppression of tumor cell metastasis and inflammatory processes, both of which are highly dependent on cell motility. SPN-1-P is far less cytotoxic than SPN, DMS, or TMS, and therefore is anticipated to be more useful for clinical application than SPN, DMS, TMS or other SPN derivatives.

Methods of Inhibiting Tumor Cell Chemotactic Motility and Tumor Cell Chemoinvasion The present invention provides a method of inhibiting tumor cell chemotactic motility comprising contacting the tumor cells with an inhibitory amount of an agent selected from the group consisting of SPN-1-P, derivatives of SPN-1-P and mimetics of the SPN-1-P or of the derivatives.

Additionally, the present invention provides a method of inhibiting tumor cell chemoinvasion comprising contacting the tumor cells with an inhibitory amount of an agent selected from the group consisting of SPN-1-P, derivatives of SPN-1-P and mimetics of the SPN-1-P or of the derivatives.

The inhibitory amount of agent used in each method can readily be determined by the assays using transwell plates described below.

As a general guideline, an inhibitory amount of SPN-1-P sufficient to inhibit tumor cell chemotactic motility and chemoinvasion is from about $10^{-8}$M to about $10^{-7}$M.

Figure 6:
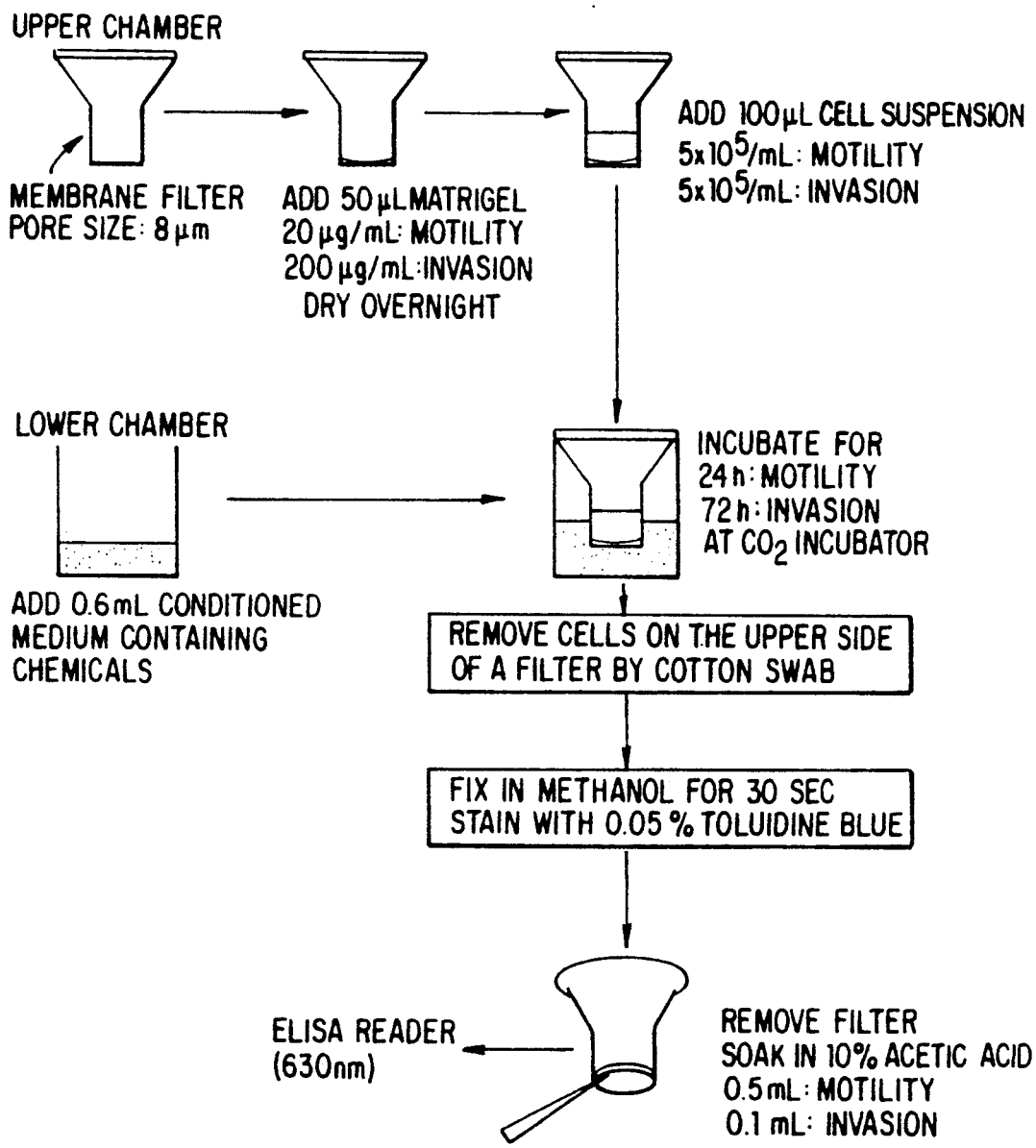
FIG. 6 depicts a scheme for chemotactic cell motility and chemoinvasion assays.
Figure 7:
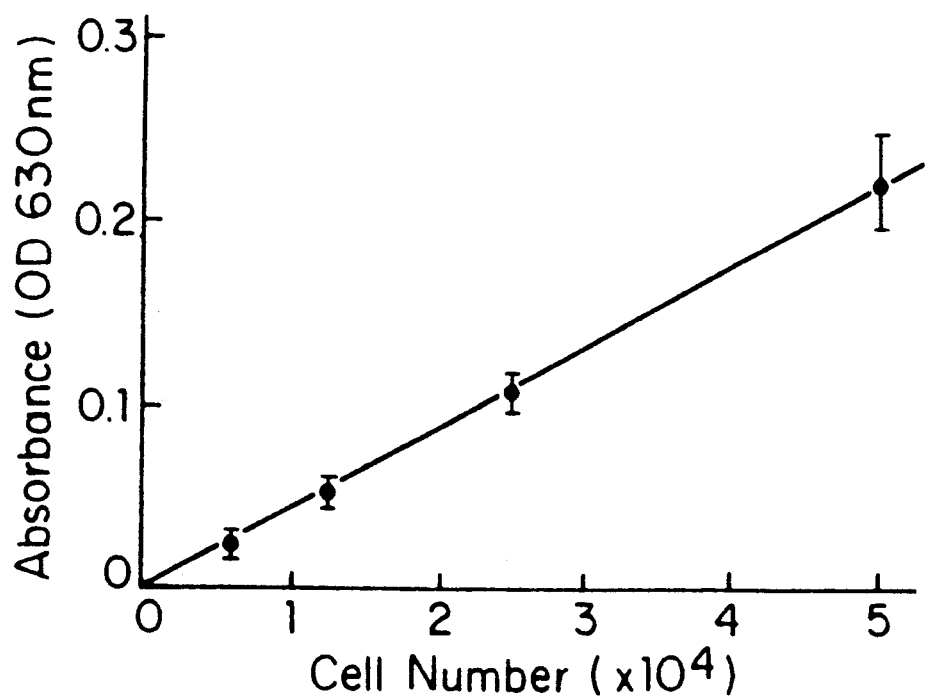
FIG. 7 is a graph showing the linear relationship between cell number and toluidine blue optical density for an assay detecting chemotactic cell motility or chemoinvasion.

The assays for determining chemotactic cell motility and chemoinvasion can be performed using transwell plates with a polycarbonate membrane filter (pore size 8 μm) (Costar Scientific, Cambridge, Mass.). Aliquots, e.g., 50 μl, of an aqueous solution of MATRI-GEL (Collaborative Research, Bedford, Mass.) containing SPN-1-P or other inhibitor (e.g., 20 μg/ml for chemotactic motility assay or 200 μg/ml for chemoinvasion assay), is added to each well and dried overnight. The filter is then fitted onto the lower chamber plate. The lower chamber can contain conditioned medium (CM) (i.e., medium used for splenic stromal cell culture, and containing motility factor secreted by these cells), e.g., 0.6 ml, with or without SPN-1-P or other inhibitor. To the upper chamber is added, e.g., about 100 μl, of cell suspension ($5 \times 10^4$ cells/ml for invasion assay, $5 \times 10^5$ cells/ml for motility assay), which is then incubated in 5% $CO_2$ at 37° C. for 70-72 hours (invasion assay) or 20 hours (motility assay). After incubation, cells remaining in the upper chamber are wiped off with a cotton swab, and cells which had migrated to the lower chamber side of the filter are fixed in methanol for 30 seconds and stained with 0.05% toluidine blue. The filter is removed, the stain is solubilized in 10% acetic acid (e.g., 0.1 ml for invasion assay, 0.5 ml for motility assay), and color intensity (optical density) is quantitated by ELISA reading at 630 nm. A schematic summary of this procedure is shown in FIG. 6. Using SPN-1-P, a linear relationship was observed between cell number and toluidine blue optical density (FIG. 7).

Method of Inhibiting Phagokinetic Activity of Tumor Cells and Neutrophils

The present invention also provides a method of inhibiting phagokinetic activity of tumor cells and neutrophils comprising contacting the cells with a phagokinetic inhibitory amount of an agent selected from the group consisting of SPN-1-P, derivatives of SPN-1-P and mimetics of the SPN-1-P or of the derivatives.

The inhibitory amount of agent can readily be determined by assays known in the art, such as the gold sol-coated plate assay described below. Using this assay, phagokinetic inhibitory amounts of SPN-1-P for tumor cells range from about 0.1 μM to about 1.0 μM, and phagokinetic inhibitory amounts of SPN-1-P for neutrophils range from about 0.45 μM to about 4.5 μM.

Phagokinetic activity is measured by the ability of cells to ingest foreign particles while moving. Cell motility can be estimated as the area of a phagokinetic track on gold sol particle-coated plates as previously described {Albrecht-Buehler, Cell, 11:395 (1977)}. A uniform coating of gold particles is prepared on glass coverslips precoated with bovine serum albumin, and coverslips are rinsed repeatedly to remove non-adhering or loosely-adhering gold particles. Freshly-prepared neutrophils or tumor cells detached from culture are placed in a Petri dish containing the gold sol-coated plate, and incubated for about 2 hours (for human neutrophils) or about 18 hours (for tumor cells). The coverslips are fixed for 1 hour in a 4% formaldehyde solution in phosphate-buffered saline (PBS) and mounted on microscope slides. The phagokinetic tracks are observed on a television connected to a light microscope (Nikon, Tokyo, Japan). Tracks on the television are transferred to translucent sheets, which are then photocopied. Phagokinetic activity is quantitated by cutting and weighing the swept area in the copy.

Method of Inhibiting Tumor Cell Metastasis and Method of Inhibiting Inflammation The above-described assays establish that SPN-1-P adversely affects motility properties of tumor cells and neutrophils. SPN-1-P is clearly demonstrated to have a strong inhibitory effect on motility of both types of cells. Because the processes of tumor cell invasion and inflammation are dependent on the motility properties of tumor cells and neutrophils, respectively, SPN-1-P, its derivatives and mimetopes of SPN-1-P or its derivatives are expected to be useful in the suppression of tumor metastasis and in the inflammatory process.

For comparison purposes, the same test cells used in the above-described assays were also exposed to numerous other sphingolipids and SPN-1-P demonstrated unexpectedly superior inhibition of both chemotactic motility and chemoinvasion as shown in Table IV in Example II below.

In addition, the inhibitory effect of SPN-1-P on chemotactic motility through MATRI-GEL-coated polycarbonate filters of mouse melanoma B16/F1 and B16/F10 cells, mouse Balb/c 3T3 fibroblasts and human fibrosarcoma HT1080 cells was compared. The results, as shown in Table V in Example II below, establish that susceptibility of B16/F1 and B16/F10 cells to sphingosine-1-phosphate was high, whereas as that of human fibrosarcoma HT1080 cells was low.

Also, for comparison purposes, B16/F10 melanoma cells were exposed to SPN and TMS in the assay to determine phagokinetic activity. As shown in Table VI in Example III below, addition of SPN or TMS to the culture medium reduced the area cleared by tumor cells. In particular, however, the average cleared area was greatly reduced when SPN-1-P was added at a concentration of 1.0 or even 0.1 μM.

Phagokinetic activity of human neutrophils was, for comparison purposes, also determined using SPN, TMS, phosphoethanolamine, and ceramide. As shown in Table VII in Example III below, the reduction in phagokinetic activity of human neutrophils was most striking for SPN-1-P and TMS.

Effects of SPN derivatives on protein kinase C activity and cell growth of B16/F1 cells was also investigated. SPN-1-P had no inhibitory effect on PKS activity of B16/F1 cells, even at 75 μM, whereas both SPN and TMS showed a strong inhibitory effect at this concentration (Table I). TMS and SPN showed, respectively, a strong and a moderate growth-inhibitory effect on B16/F1 cells at 10 μM, whereas SPN-1-P showed no growth-inhibitory effect at this concentration (Table II). Toxicity of these compounds to B16/F1 cells and human neutrophils was also examined using a trypan blue exclusion assay after 1 hour incubation with the compounds. SPN-1-P showed weak toxicity against both types of cells at 45-50 μM, whereas SPN was very toxic at this concentration (Table III).

TABLE I

| Effect of SPN derivatives on PKC activity of B16/F1 melanoma cells. | | |
|---|---|---|
| Compound | Conc. (μM) | % PKC activity |
| Control |  | 100 ± 11 |
| SPN | 75 | 34 ± 7 |
| SPN-1-P | 75 | 108 ± 32 |
|  | 10 | 121 ± 10 |
| TMS | 75 | 16 ± 3 |

*Mean ± S.E. (n = 3). For controls (defined as 100%), PKC activity was 33225 cpm per tube per 20 min, as measured by $^{32}P$ incorporation into histone III-S.

TABLE II

| Effect of SPN derivatives on growth of B16/F1 melanoma cells. | | |
|---|---|---|
| Compound | Conc. (μM) | % Growth |
| Control |  | 100 ± 4 |
| SPN | 10 | 78 ± 4* |
|  | 5 | 87 ± 10 |
|  | 1 | 101 ± 1 |
| SPN-1-P | 10 | 87 ± 10 |
|  | 5 | 96 ± 2 |

TABLE II-continued

Effect of SPN derivatives on growth of B16/F1 melanoma cells.

| Compound | Conc. (μM) | % Growth |
|---|---|---|
| | 1 | 105 ± 10 |
| | 0.1 | 97 ± 5 |
| | 0.01 | 103 ± 10 |
| TMS | 10 | 11 ± 1 |
| | 5 | 77 ± 8 |
| | 1 | 88 ± 7 |
| N-acetyl-SPN | 10 | 102 ± 4 |

*Mean ± S.E. (n = 3). For controls (defined as 100%), cell number was 5.5 ± 0.2 × $10^5$/dish. $10^5$ cells were seeded and cultured on a 35 mm plastic dish in Dulbecco's modified Eagle's medium containing 2% fetal bovine serum in the presence or absence of SPN derivatives. 48 hr later, cells were counted.

TABLE III

Toxicity of SPN derivatives on B16/F1 melanoma cells and human neutrophils.

| Cell | Compound | Conc. (μM) | Cell viability (%) |
|---|---|---|---|
| B16/F1 | control | | 99 |
| | SPN | 50 | 21 |
| | SPN-1-P | 50 | 72 |
| neutrophil | control | | 99 |
| | SPN | 45 | 5 |
| | SPN-1-P | 45 | 98 |

Figure 12A:
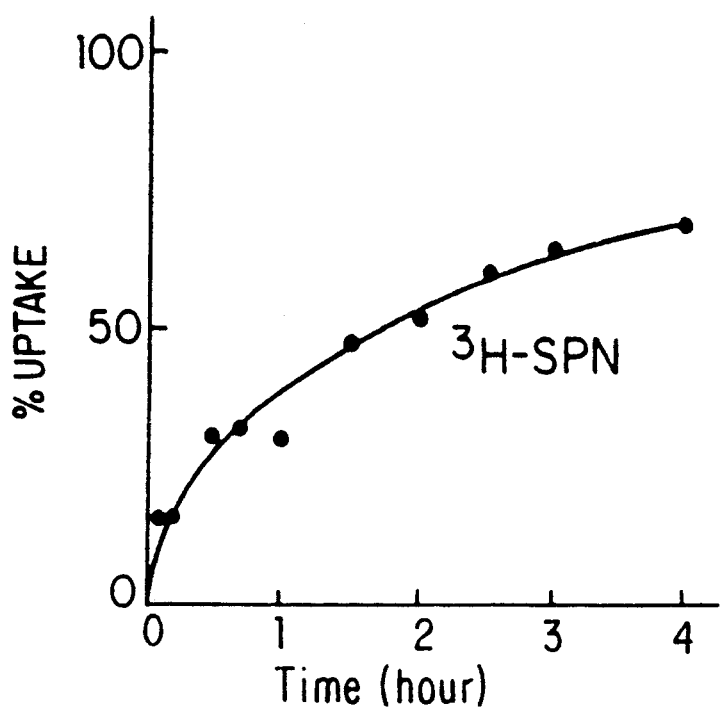
FIGS. 12A and 12B depict the time-course uptake of $^3$H-SPN (FIG. 12A) and $^{14}$C-TMS (FIG. 12B) by B16/F1 cells. The ordinate represents % radioactivity taken up by B16/F1 cells and the abscissa represents time in hours.
Figure 12B:
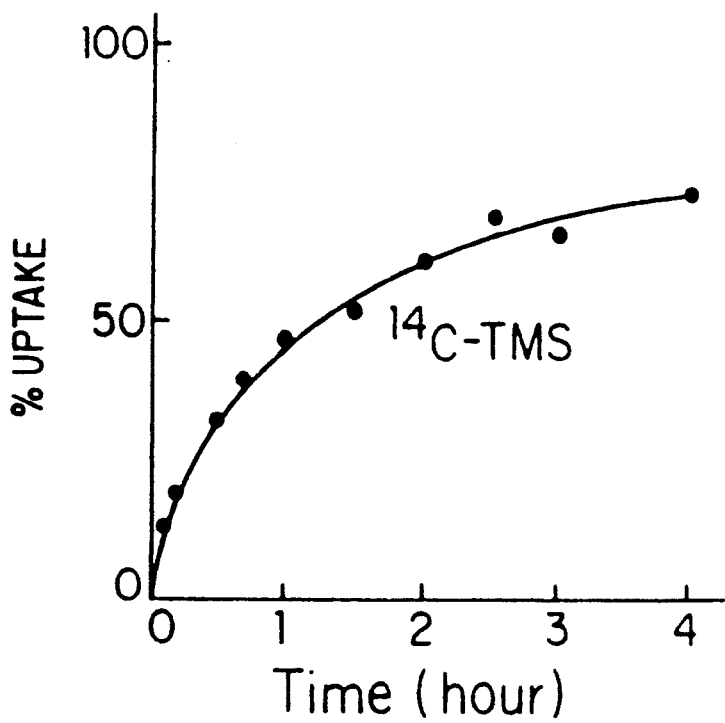
Figure 13A:
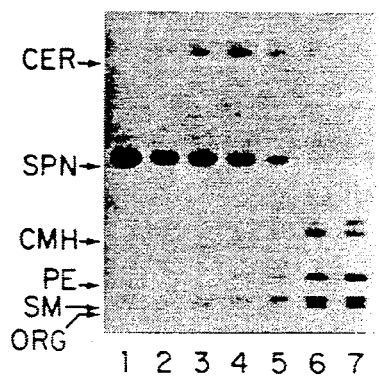
FIGS. 13A-13C depict the time-course changes in labeling of various SPN derivatives after addition of $^3$H-SPN to B16/F1 cells.
Figure 13B:
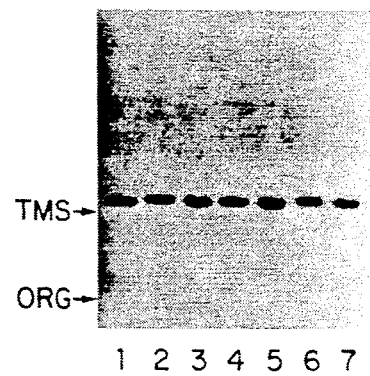
Figure 13C:
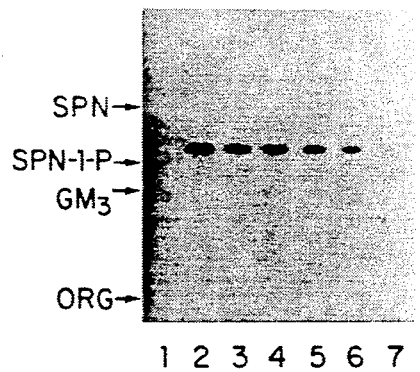

In addition, the uptake and metabolic conversion of SPN vs. TMS was investigated. Both $^3$H-labeled SPN and $^{14}$C-labeled TMS were rapidly incorporated into B16/F1 cells (FIGS. 12A and 12B). However, only SPN was rapidly converted into SPN-1-P and ceramide (CER) (FIG. 13). This was clearly demonstrated when cells were incubated with $^3$H-SPN in the presence of D-PDMP, which inhibits conversion of Cer into GlcCer and other glycosphingolipids. Rapid conversion of SPN into sphingosine-1-phosphate is clearly indicated by the appearance of bands corresponding to SPN-1-P prior to conversion into Cer. The SPN-1-P peak appeared after 10 minutes incubation, whereas the Cer peak appeared after 1 hour incubation. In contrast, although $^{14}$C-TMS was rapidly taken up by cells, the band corresponding to TMS was unchanged regardless of incubation time (FIG. 13). These findings suggest that inhibitory effects on cell motility and invasion are due to rapid conversion of SPN into SPN-1-P.

Accordingly, the present invention provides a method of inhibiting tumor cell metastasis comprising administering to a host in need of treatment a metastasis inhibitory amount of an agent selected from the group consisting of SPN-1-P, derivatives of SPN-1-P and mimetics of the SPN-1-P or of the derivatives, and pharmaceutically acceptable salts thereof.

The present invention also provides a method of inhibiting inflammation due to motility of neutrophils comprising administering to a host in need of treatment an inflammation inhibitory amount of an agent selected from the group consisting of SPN-1-P, derivatives of SPN-1-P, and mimetics of the SPN-1-P or of the derivatives, and pharmaceutically acceptable salts thereof.

A specific use of the method of inhibiting tumor cell metastasis includes treatment of malignancies. The method of inhibiting inflammation is applicable to any inflammation which is due to motility and invasion into blood vessel walls of neutrophils.

The inhibitory effective amount of SPN-1-P or other inhibitor can be determined using art-recognized methods, such as by establishing dose response curves in suitable animal models and extrapolating to human; extrapolating from suitable in vitro data, for example, as described herein; or by determining effectiveness in clinical trials.

Suitable doses of SPN-1-P or other inhibitor according to this invention depend upon the particular medical application, such as the severity of the disease, the weight of the individual, age of the individual, half-life in circulation, etc., and can be determined readily by the skilled artisan. The number of doses, daily dosage and course of treatment may vary from individual to individual.

SPN-1-P and other inhibitors can be administered in a variety of ways such as orally, parenterally and topically. Suitable pharmaceutically acceptable carriers, diluents or excipients which can be combined with SPN-1-P and other inhibitors for administration depend upon the particular medical use and can be determined readily by the skilled artisan.

The SPN-1-P or other inhibitors with or without carrier can take a variety of forms, such as tablets, capsules, bulk or unit dose powders or granules; may be contained with liposomes; or may be formulated into solutions, emulsions, suspensions, ointments, pastes, creams, gels, foams or jellies. Parenteral dosage forms include solutions, suspensions and the like.

Additionally, a variety of arr-recognized excipients, diluents, fillers, etc., are likely to be included in the dosage forms. Such subsidiary ingredients include disintegrants, binders, lubricants, surfactants, emulsifiers, buffers, moisturizers, solubilizers and preservatives. The artisan can configure the appropriate formulation comprising inhibitor and seeking guidance from numerous authorities and references such as "Goodman & Gilman's, The Pharmaceutical Basis of Therapeutics" (6 Ed., Goodman et al, MacMillan Publ. Co., N.Y. 1980).

In body sites that are characterized by continual cell growth or that require cell growth inhibition because of disfunction and that are relatively inaccessible, SPN-1-P and other inhibitors can be administered in a suitable fashion to ensure effective local concentrations. For example, the inhibitors may be injected in a depot or adjuvant, carried in a surgically situated implant or reservoir that slowly releases a fixed amount of inhibitor over a period of time or may be complexed to recognition molecules with the capability of binding to the site presenting with abnormal cell growth. An example of such a contemplated scenario is a recognition molecule that is an antibody with binding specificity for a bone marrow specific antigen wherein the marrow-specific antibody is complexed to SPN-1-P or other inhibitor, the complex being administered to a patient with leukemia.

Synthesis of Sphingosine-1-Phosphate and Its Derivatives

Various sphingosine (SPN) derivatives can be synthesized chemically as shown in FIG. 2 and FIGS. 3A, 3B, and 3C. These include sphingosine-1-phosphate (SPN-1-P): compound 1', N,N-dimethylsphingosine-1-phosphate {DMS-1-P (2)}, N,N,N-trimethylsphingosine-1-phosphate {TMS-1-P (3)}, N-acetyl and N-acylsphingosine-1-phosphate {N-acetyl and N-acyl-SPN-1-P (4)}, sphingosine-1,3-diphosphate {SPN-1,3-diphosphate (5)}, sphingosine-3-phosphate {SPN-3-P (6)}, sphingosine-1-thiophosphate {SPN-1-S-P (7)}, N,N-dimethylsphingosine-1-thiophosphate {DMS-1-S-P (8)}, and N,N,N-trimethylsphingosine-1-thiophosphate {TMS-1-S-P (9)}. The synthesis methods that are described below are conventional in the art and can be readily practiced by the skilled artisan.

Synthesis of Sphingosine-1-Phosphate (Compound 1)

Figure 3A:
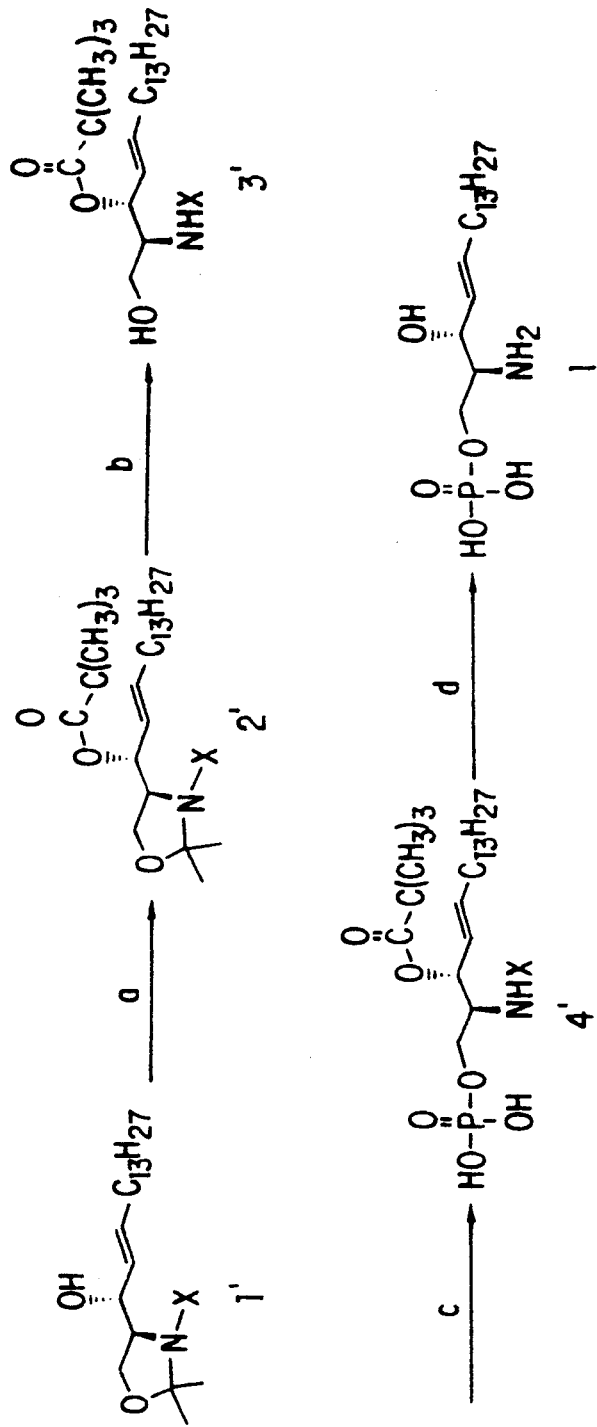
FIGS. 3A–3C depict chemical synthesis of SPN-1-P and its various derivatives.
Figure 3B:
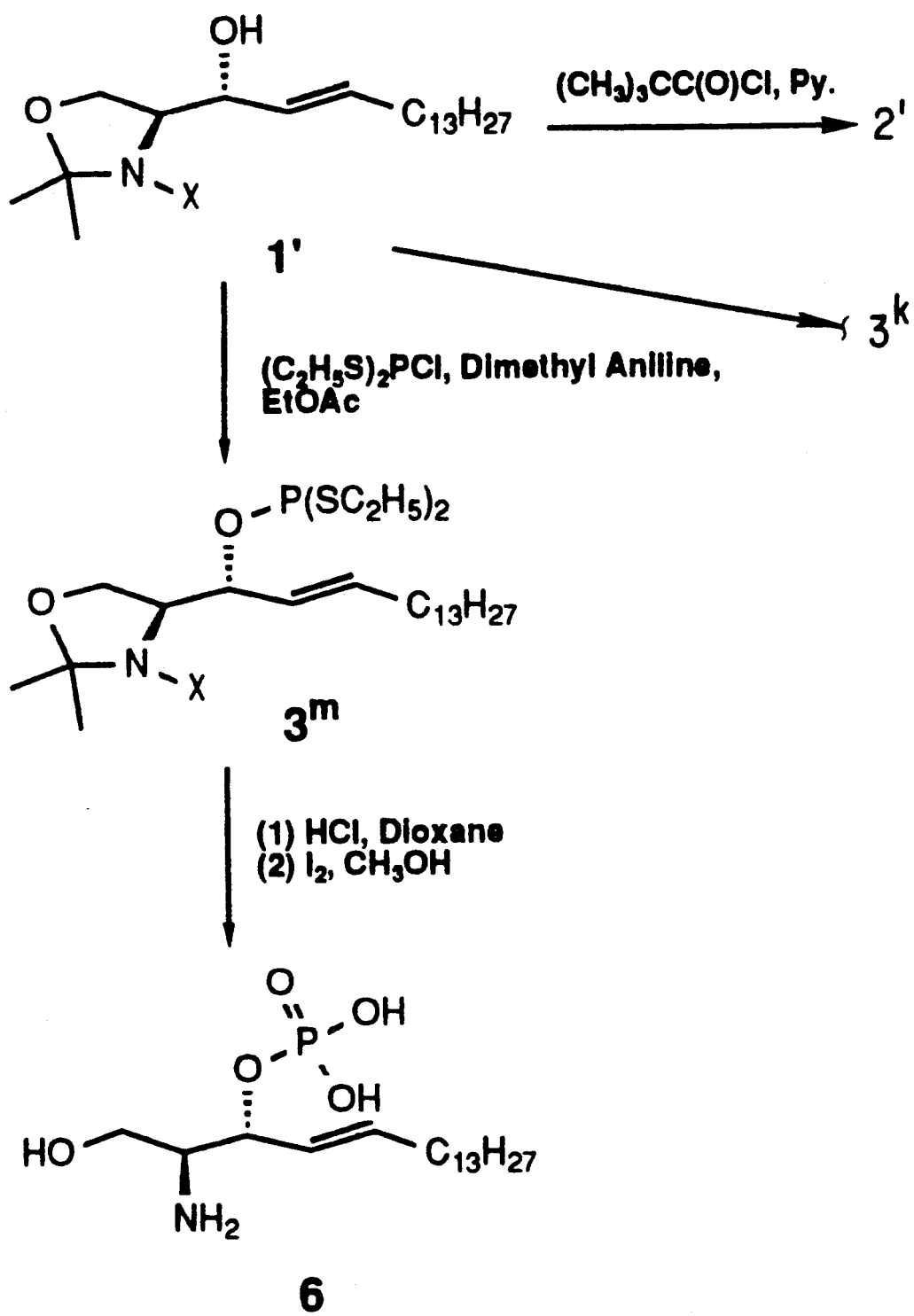
Figure 3C:
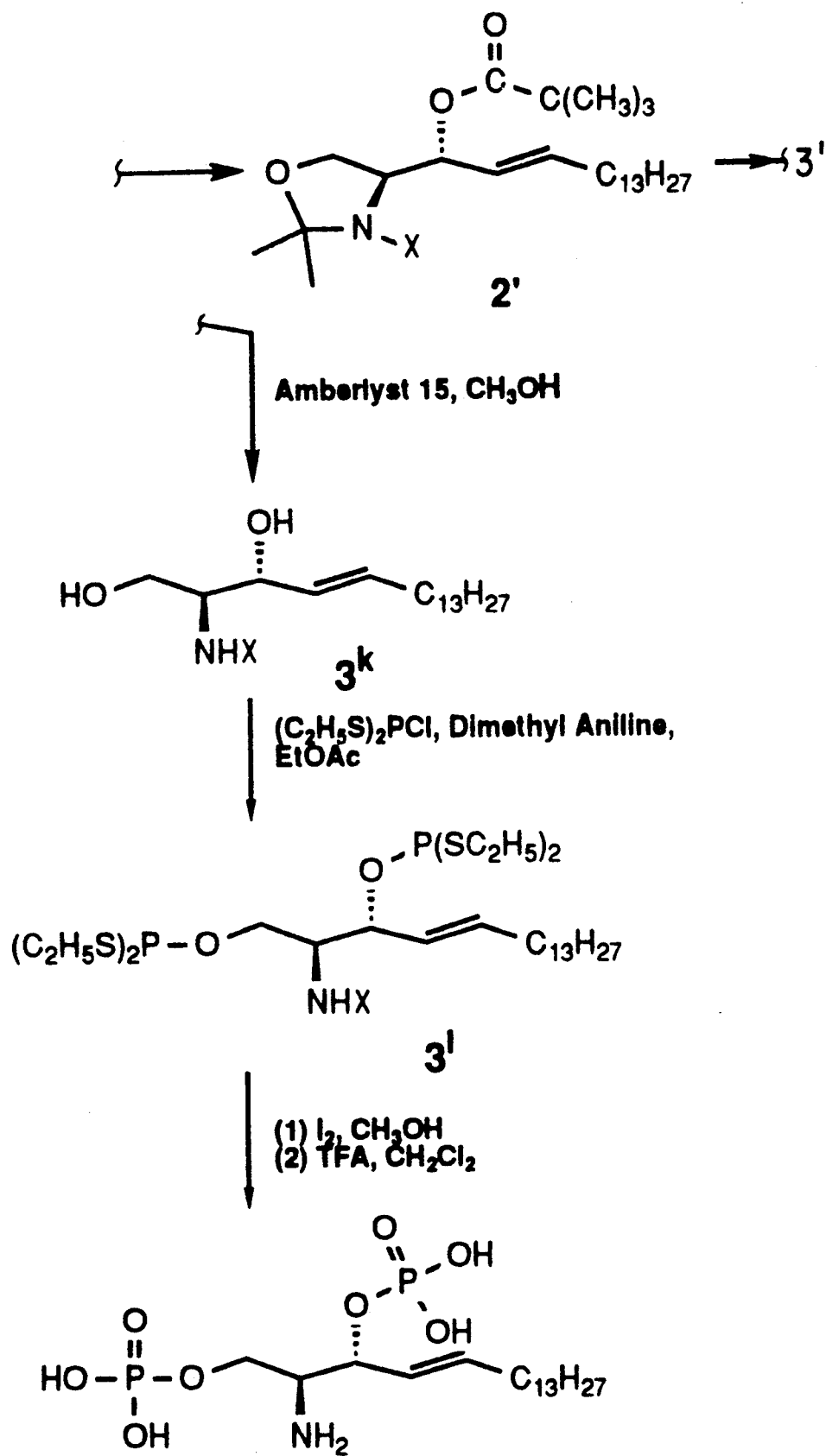
Figure 3D:
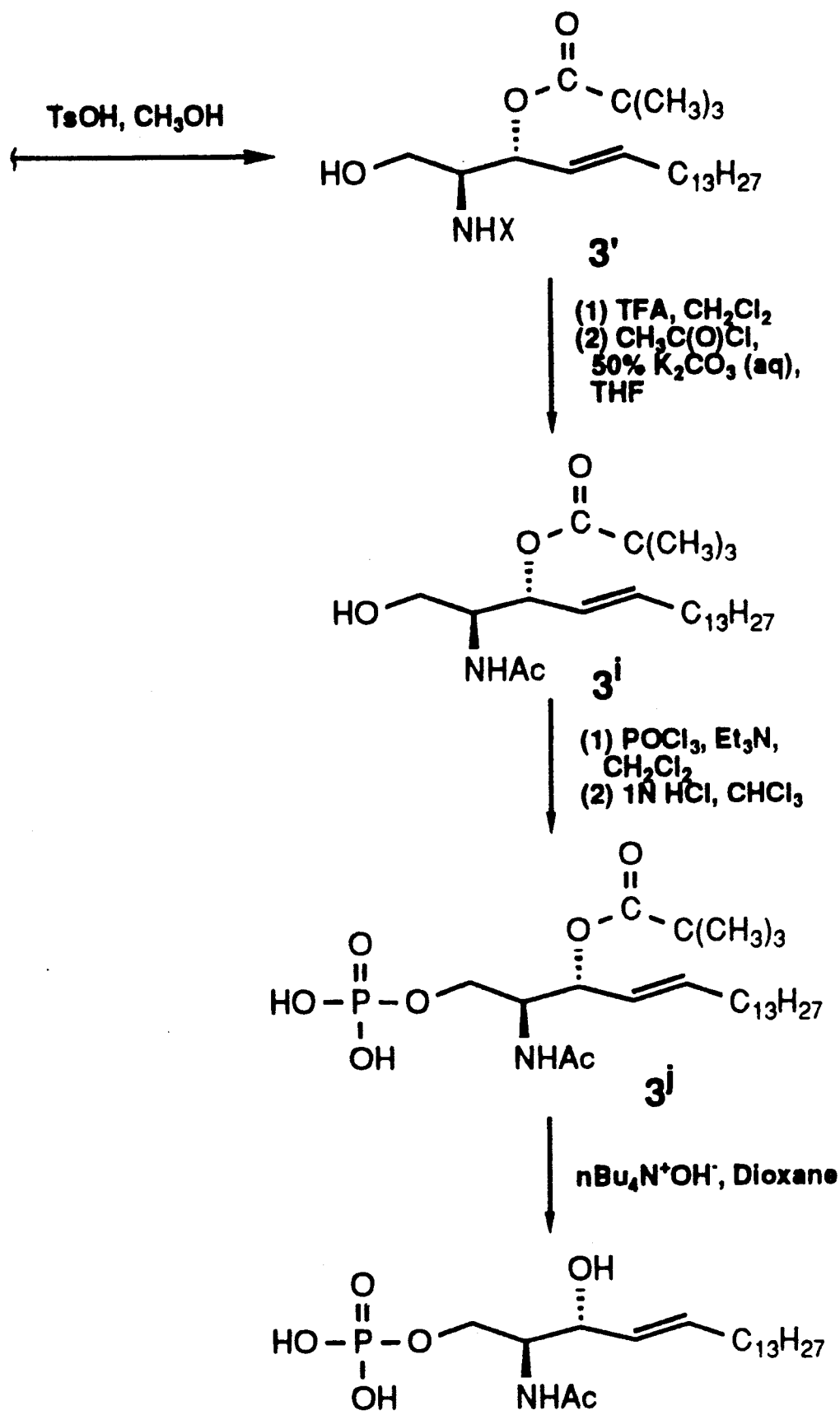
Figure 3E:
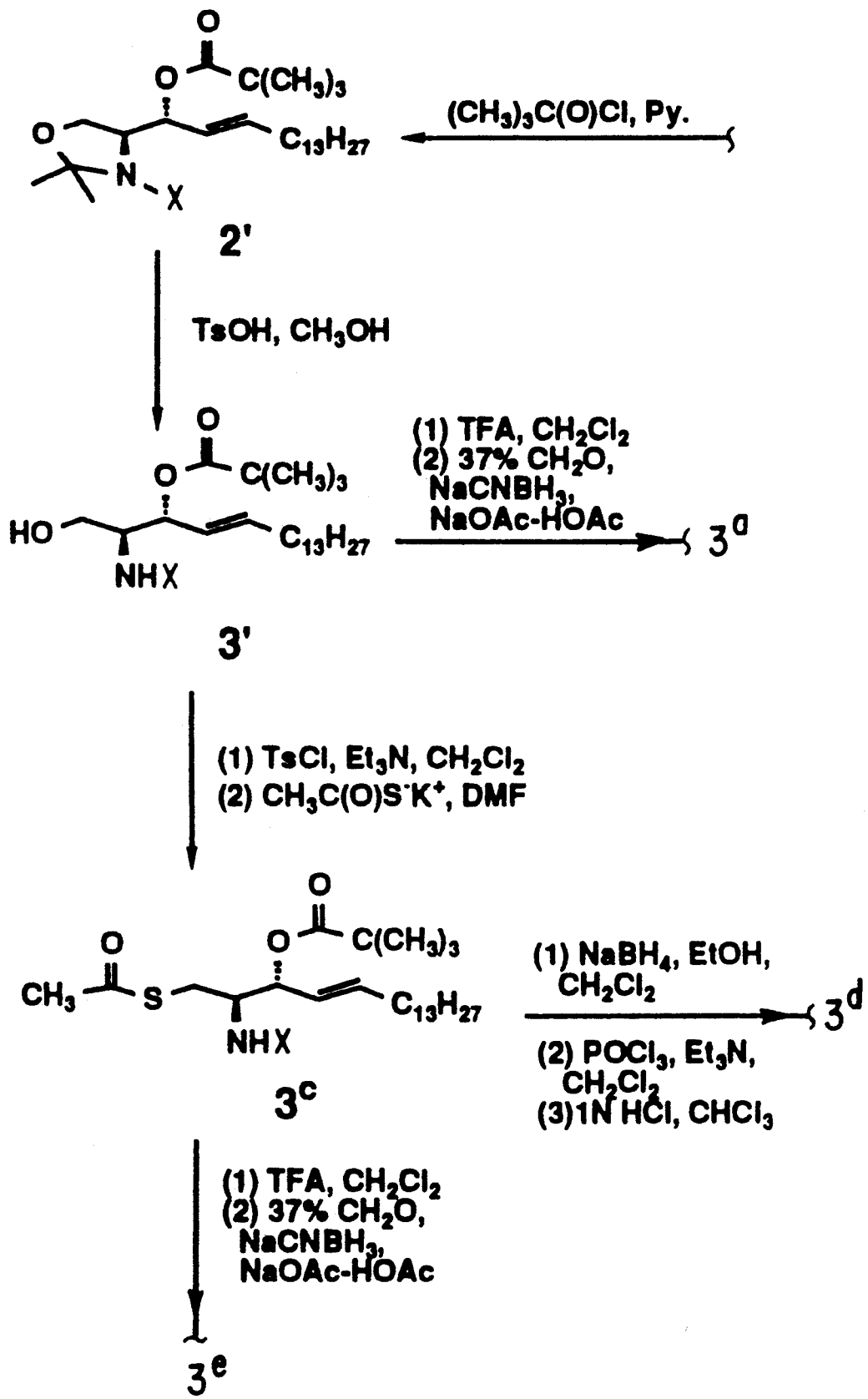
Figure 3F:
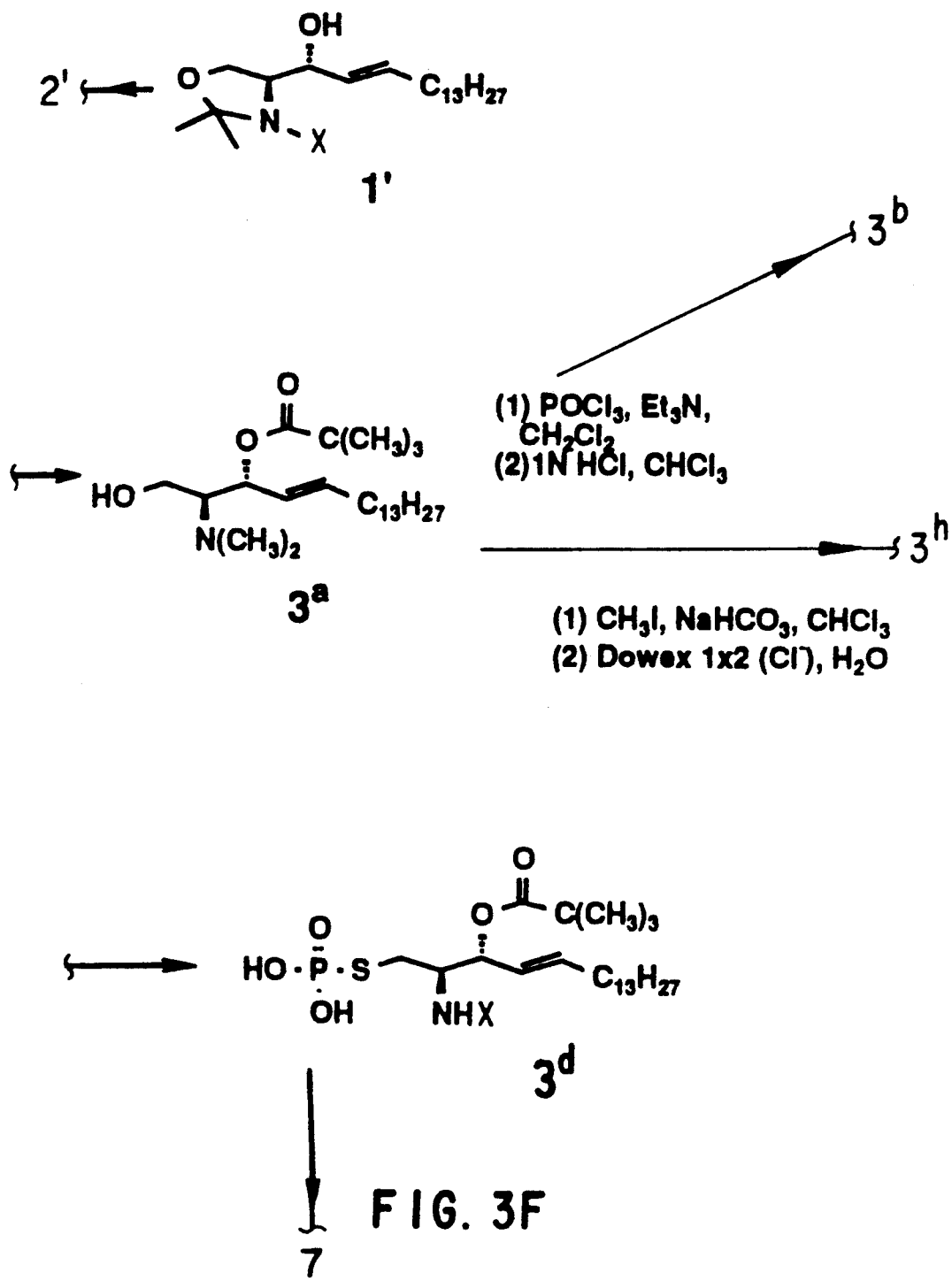
Figure 3G:
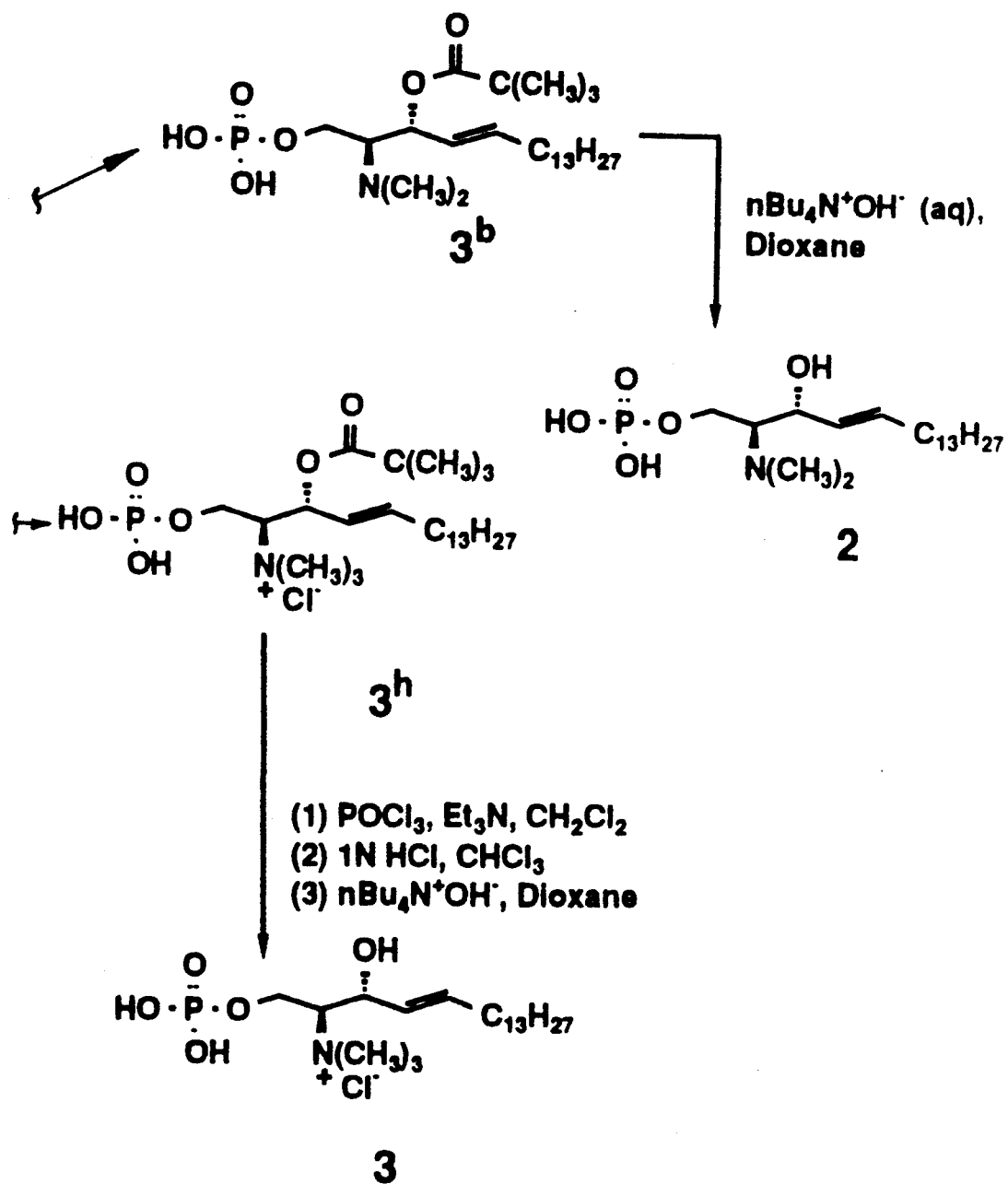
Figure 3H:
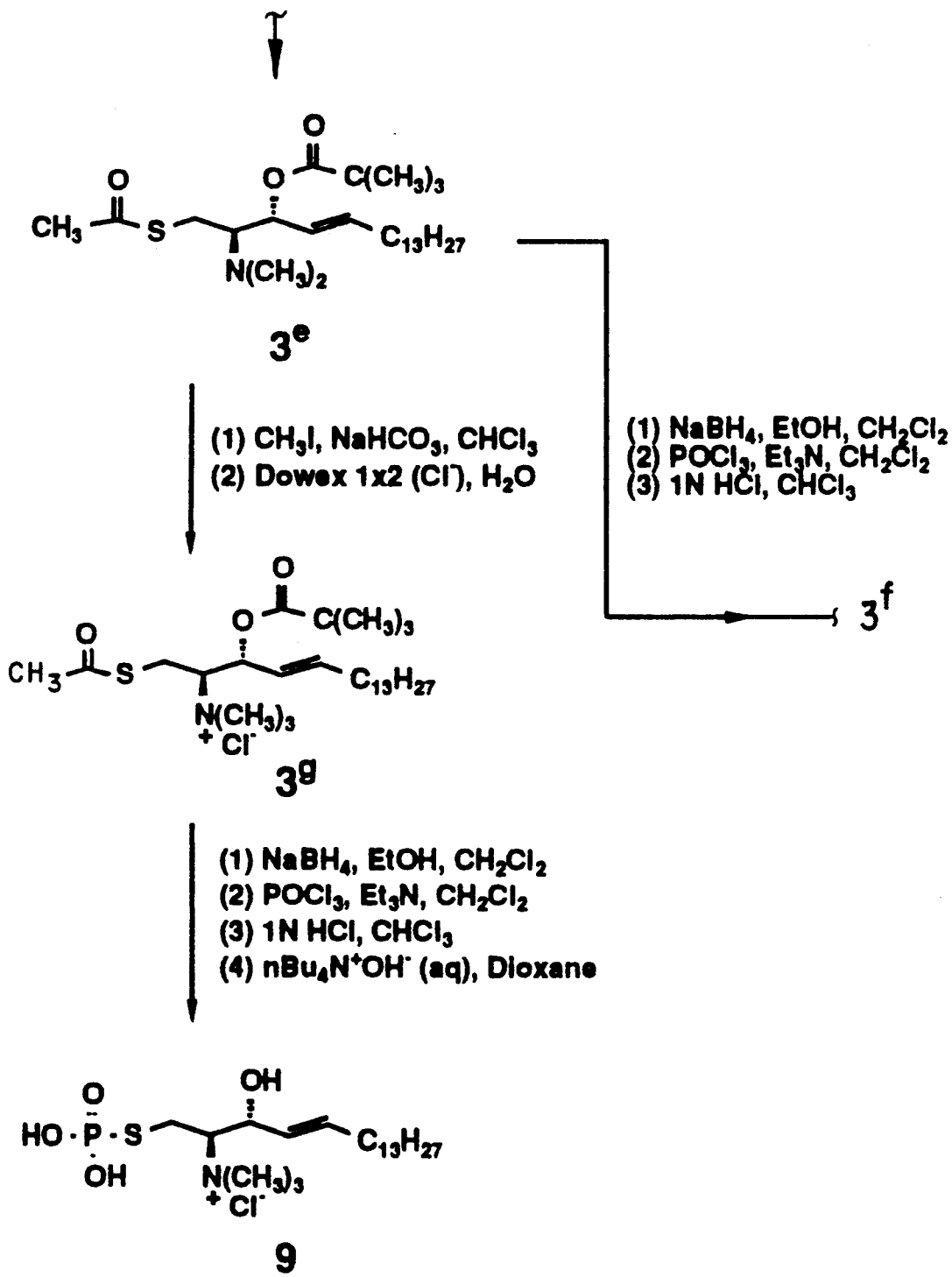
Figure 3I:
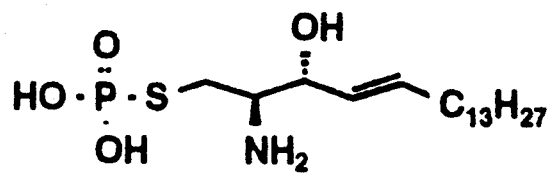
Figure 3I:
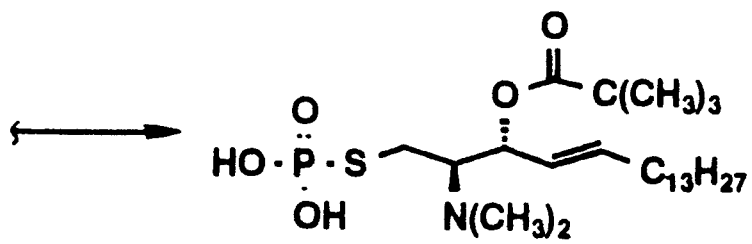
Figure 3I:
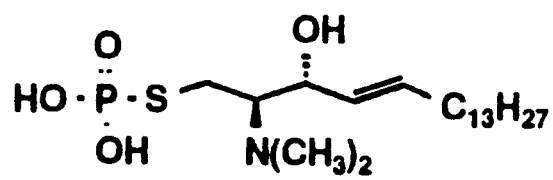

FIG. 3A summarizes the new procedure for synthesis of SPN-1-P (1), starting with the protected SPN (1') prepared from previously-known procedures {Garmer P., Park J. M., J. Org. Chem., 52:2361 (1987); Herold P., Helvetica Chimica Acta, 71:354 (1988); Radunz H. E., Devant R. M., Eiermann V., Liebigs Ann. Chem., 1988:1103 (1988)}. In compound 1', X is a protecting group such as N-tert-butyloxycarbonyl (t-Boc). 2-N-X-3-0-pivaloyl-D-erythro-SPN (3') is prepared by esterification of C-3 OH group of compound 1', for example with pivaloyl chloride in dry pyridine, to give compound 2', followed by selective deprotection of the primary hydroxyl group, for example with p-toluenesulfonic acid (p-TsOH) in methanol (MeOH). Phosphorylation of the primary hydroxyl group of compound 3', for example with phosphorus oxychloride in the presence of triethylamine and $CH_2Cl_2$ (distilled from $CaH_2$) followed by hydrolysis, for example with 1N HCl in $CHCl_3$, yields 2-N-X-3-0-pivaloyl-D-erythro-SPN-1-P (compound 4'). Deprotection of the C-3 OH group (e.g., with $nButN^+OH^-$[aq]/dioxane) and the amino group (e.g., with TFA/$CH_2Cl_2$) respectively gives the desired SPN-1-P (Compound This synthetic product can be proven to be identical to that derived from sphingosylphosphocholine in the $^1$H-NMR spectrum (500 MHz) and mass spectrum (negative FAB, DMIX as matrix), which are shown in FIGS. 4 and 5. The small difference in NMR spectrum reflects the fact that enzymatically-synthesized SPN-1-P contains a small amount of L-threo isomer, whereas chemically-synthesized SPN-1-P does not contain any detectable amount of L-threo isomer. Thus, chemically-synthesized SPN-1-P, according to the present invention, is essentially free of L-threo isomer as detected by NMR spectroscopy.

Synthesis of N,N-Dimethylsphingosine-1-Phosphate (Compound 2)

Compound 3' is treated, e.g., with trifluoroacetic acid (TFA) and $CHCl_2$, to eliminate the precting moiety X, and then reductive methylation is carried out, e.g., in the presence of 37% $CH_2O$ and $NaCNBH_3$ in sodium acetate aqueous buffer, resulting in compound 3''. Compound 3'' is then phosphorylated, e.g., with $POCl_3$ in triethylamine ($Et_3N$) and $CH_2Cl_2$, and the Cl atom is replaced with an OH group by treatment, e.g., with 1N HCl in $CHCl_3$, resulting in compound $3^b$. The pivaloyl group at the C-3 OH is eliminated, e.g., by treatment in tetrabutylammonium hydroxide ($nBu_4N^+OH^-$) in aqueous dioxane, resulting in compound 2.

Synthesis of N,N,N-Trimethylsphingosine-1-Phosphate (Compound 3)

Compound $3^a$ is permethylated, e.g., with $CH_3I$ and $NaHCO_3$ in $CHCl_3$, followed by DOWEX 1×2 ($Cl^-$) treatment to give compound $3^h$. Next, the C-1 OH is phosphorylated, e.g., with $POCl_3$ in $Et_3N$ and $CH_2Cl_2$, followed by replacement of Cl by an OH group by treatment, e.g., with 1N HCl and $CHCl_3$. Next, the pivaloyl group is eliminated, e.g., by treatment in the presence of $nBu_4N^+OH^-$ in aqueous dioxane, resulting in compound 3.

Synthesis of Sphingosine-1-Thiophosphate (Compound 7)

Compound 3' is treated with tosyl chloride (TsCl) in $Et_3N$ and $CH_2Cl_2$, followed by treatment with potassium thioacetate in N,N-dimethylformamide (DMF) to yield compound $3^c$. The acetyl group is removed by treatment with $NaBH_4$ in ethanol (EtOH) and $CH_2Cl_2$. Next, the SH group is phosphorylated, e.g., with $POCl_3$ in $Et_3N$ and $CH_2Cl_2$ followed by treatment in 1N HCl in $CHCl_3$, to yield compound $3^d$. Compound $3^d$ is treated, e.g., with $nBu_4N^+OH^-$ in aqueous dioxane to eliminate the pivaloyl group at the C-3 OH. Next, X is eliminated, e.g., with TFA in $CH_2Cl_2$, to yield compound 7.

Synthesis of N,N-Dimethyl-Sphingosine-1-Thiophosphate (Compound 8)

Compound $3^c$ is treated, e.g., with TFA in $CH_2Cl_2$ to eliminate the protecting group X (e.g., t-Boc), and reductive methylation is carried out, e.g., with 37% $CH_2O$ and $NaCNBH_3$ in aqueous acetate buffer, to replace the amino group with an N-dimethyl group, yielding compound $3^e$. Compound $3^e$ is treated with $NaBH_4$ in EtOH and $CH_2Cl_2$, followed by phosphorylation, e.g., with $POCl_3$ in $Et_3N$ and $CH_2Cl_2$, and treatment with 1N HCl in $CHCl_3$ to yield compound $3^f$. Compound $3^f$ is treated, e.g., with $nBu_4N^+OH^-$ in aqueous dioxane, to eliminate the pivaloyl group at the C-3 OH, yielding compound 8.

Synthesis of N,N,N-Trimethylsphingosine-1-Thiophosphate (Compound 9)

Compound $3^e$ is treated, e.g., by Purdie permethylation with $CH_3I$, $NaHCO_3$, and $CHCl_3$, followed by treatment with DOWEX 1×2 ($Cl^-$), to yield compound $3^g$. Compound $3^g$ is treated, e.g., with $NaBH_4$, EtOH, and $CH_2Cl_2$, to create an SH group at the 1-position of sphingosine. Next, the SH group is phosphorylated, e.g., with $POCl_3$ in $Et_3N$ and $CH_2Cl_2$, followed by replacement of Cl with an OH group, e.g., by treatment with 1N HCl and $CHCl_3$, followed by treatment, e.g., with $nBu_4N^+OH^-$ in aqueous dioxane, to eliminate the pivaloyl group at the C-3 OH, yielding compound 9.

Synthesis of N-Acetylsphingosine-1-Phosphate (Compound 4)

Compound 3' is treated, e.g., with TFA in $CH_2Cl_2$, to eliminate the protecting group X (e.g., t-Boc), and then treated, e.g., with $CH_3(CH_2)_nCOCl$ (n=0 to 22) in 50% $K_2CO_3$ {in aqueous tetrahydrofuran (THF)} to acetylate or acylate the ammonium group to yield compound $3^i$. Compound $3^i$ is treated, e.g., with $POCl_3$ in $Et_3N$ and $CH_2Cl_2$ and then with 1N HCl in $CHCl_3$, to phosphorylate the C-1 OH group to yield compound $3^j$. Compound $3^j$ is then treated, e.g., with $nBu_4N^+OH^-$ in aqueous dioxane to eliminate the pivaloyl group at the C-3 OH yielding compound 4.

Synthesis of Sphingosine-1,3-Diphosphate (Compound 5)

Compound 1' is treated, e.g., with AMBERLYST number 15 in $CH_3OH$, to selectively deprotect the C-1 OH group in order to yield compound $3^k$. Compound $3^k$ is then treated with $(C_2H_5S)_2PCl$ in dimethyl aniline and ethyl acetate (EtOAc) in order to form a $P(SC_2H_5)_2$ group at the C-3 hydroxyl and at the C-1 hydroxyl to give compound $3^1$. Compound $3^1$ is then treated, e.g., with $I_2$ in $CH_3OH$ and then with TFA in $CH_2Cl_2$ in order to phosphorylate the C-1 OH and the C-3 OH and deprotect the amino group to give compound 5.

Synthesis of Sphingosine-3-Phosphate (Compound 6)

Compound 1' is treated with $(C_2H_5S)_2PCl$ in dimethyl aniline and EtOAc to form a $P(SC_2H_5)_2$ group at the C-3 hydroxyl to give compound $3^m$. Compound $3^m$ is then treated, e.g., with HCl in dioxane and then with $I_2$ in $CH_3OH$, in order to phosphorylate the C-3 hydroxyl and deprotect the C-1 OH and the amino group to give compound 6.

The invention will now be described by reference to specific examples which are not meant to be limiting. Unless otherwise specified, all percents, ratios, etc., are by volume.

EXAMPLES

EXAMPLE I

PREPARATION OF SPHINGOSINE-1-PHOSPHATE

Sphingosine-1-phosphate (SPN-1-P) was synthesized both enzymatically and chemically.

Enzymatic synthesis was achieved through degradation of sphingosylphosphocholine by phospholipase D as previously described {Veldhoven et al, J. Lipid Res., 30:611 (1989)}.

FIG. 3A summarizes the procedure for chemical synthesis of SPN-1-P, starting with the protected SPN-1 (1') prepared from previously-known procedures {Garmer P., Park J. M., J. Org. Chem., 52:2361 (1987); Herold P., Helvetica Chimica Acta, 71:354 (1988); Radunz H. E., Devant R. M., Eiermann V., Liebigs Ann. Chem., 1988:1103 (1988)}. For purposes of this example, the protected SPN-1 was protected with N-tert-butyloxycarbonyl (t-Boc). Synthesis of the compound 2', 0.22 g (94%), as a colorless oil, was accomplished by esterification of the C-3 OH group of the protected sphingosine 1' (0.20 g, 0.46 mmol) with pivaloyl chloride (1.0 ml, 8.1 mmol) in 5 ml of dry pyridine at 25° C. for 4 h, which was purified by silica-gel chromatography (EtOAc/hexane, (1:8 v:v)). Selective deprotection of the C-1 OH group of 2' (0.21 g, 0.40 mmol) by treatment with p-toluenesulfonic acid (~100 mg), in 10 ml of methanol at 25° C. for 5 h afforded 2-N-t-Boc-3-O-pivaloyl-D-erythro-SPN (3'), 0.135 g (70%), as a colorless oil (silica gel chromatography, EtOAc/hexane (1:4 v:v)). Phosphorylation of the C-1 hydroxyl group of compound 3 (14 mg, 0.029 mmol) with phosphorus oxychloride (26 µl, 0.27 mmol) in the presence of triethylamine (43 µl, 0.3 mmol) and 0.5 ml of $CH_2Cl_2$ (distilled from $CaH_2$) at 25° for 2 h followed by hydrolysis with 1 ml of 1N HCl and 1 ml of $CHCl_3$ (25° C., 1.5 h) yielded 12.9 mg (80%) of 2-N-t-Boc-3-O-pivaloyl-D-erythro-SPN-1-P (compound 4') (silica gel chromatography with $CH_2Cl_2/CH_3OH/AcOH$, 6:1:0.2, v:v:v). Finally, deprotection of the C-3 OH group of the compound 4' (12.9 mg, 0.023 mmol) ((1) 35 drops of 40 wt% $nBu_4N^+OH^-$(aq.)/3 ml of dioxane, 4 h, 25° C.; (2) AMBERLITE IR-120, $H_2O$) followed by removal of the amino protecting group (8 ml 50% $TFA/CH_2Cl_2$, 0.5 h, 25° C.) gave the desired SPN-1-P, 10 mg (77%), as a white solid (HOAc as a counterion), which was purified by silica gel chromatography ($nBuOH/H_2O/AcOH$, 6:1:1, v:v:v).

This synthetic product proved identical to that derived from sphingosylphosphocholine in the H-NMR spectrum (500 MHz) and mass spectrum (negative FAB, DMIX as matrix), which are shown in FIGS. 4 and 5.

Figure 4A:
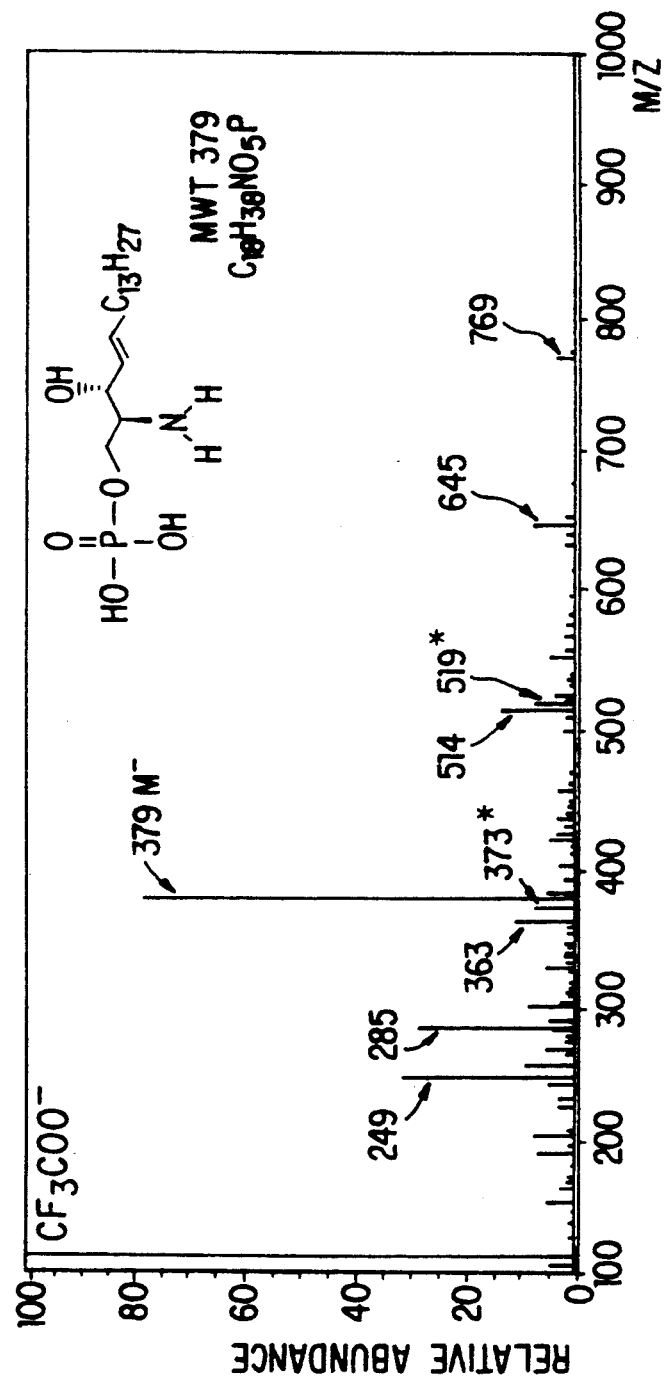
FIGS. 4A and 4B are negative ion fast atom bombardment mass spectra (DMIX as matrix) of SPN-1-P made from sphingosylphosphocholine with phospholipase D (FIG. 4A) and of SPN-1-P chemically synthesized (FIG. 4B).
Figure 4B:
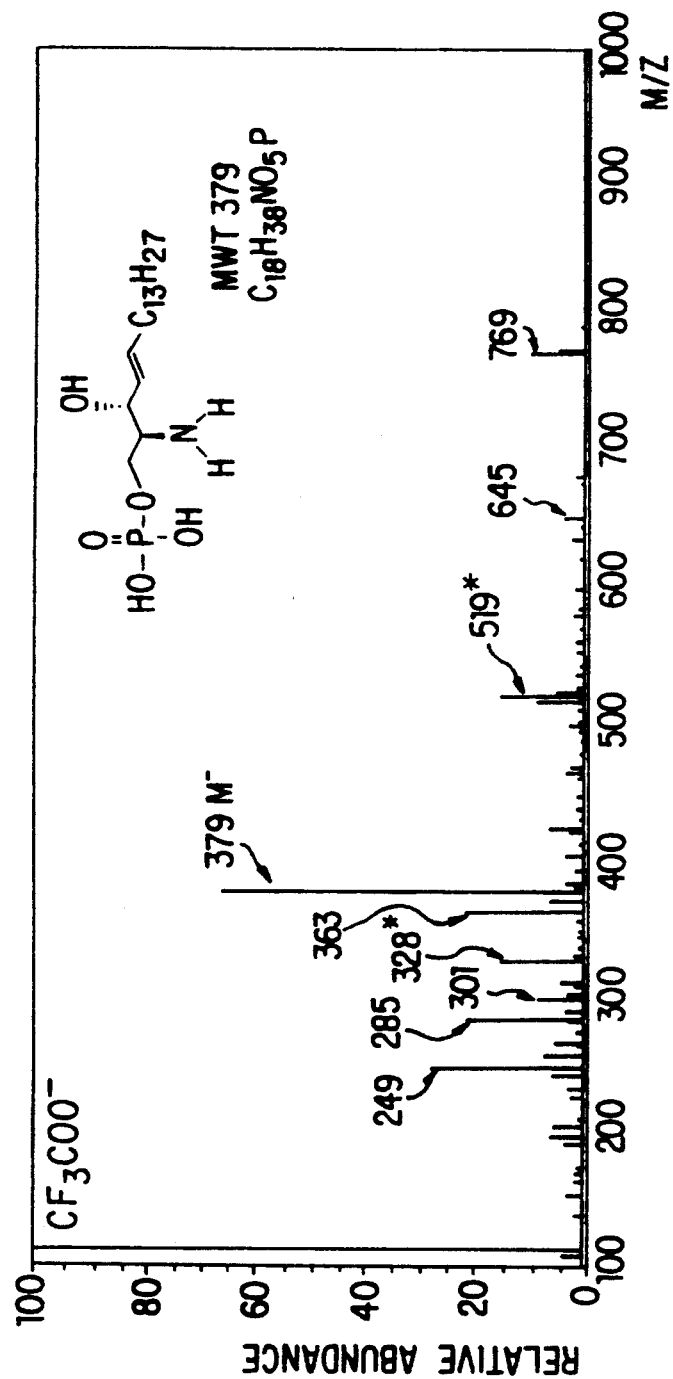

FIGS. 4A and 4B show negative ion fast atom bombardment mass spectra (DMIX as matrix) of SPN-1-P made from sphingosylphosphocholine with phospholipase D (FIG. 4A) and of SPN-1-P chemically synthesized (FIG. 4B).

Figure 5A:
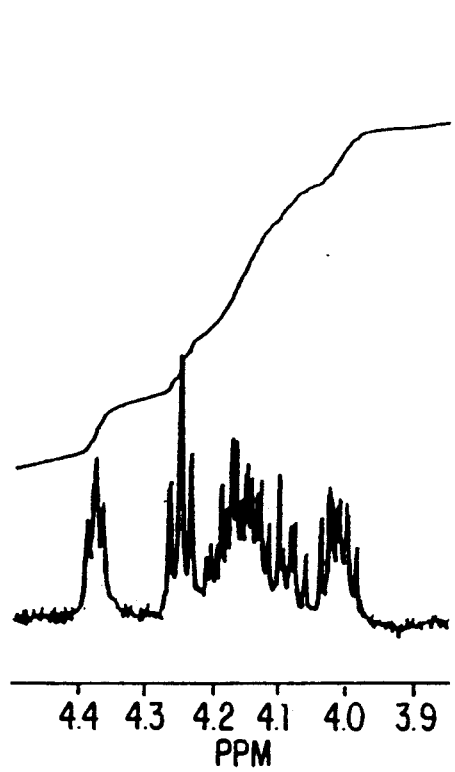
FIGS. 5A-D, are portions of the $^1$H-NMR spectra (500 MHz) of SPN-1-P made from sphingosylphosphocholine with phospholipase D (FIGS. 5A and 5B) and of SPN-1-P chemically synthesized (FIGS. 5C and 5D). The spectra were taken in methyl-$^{12}$C-d$_3$-alcohol-d-acetic-d$_3$-acid-d 8:2 (v/v).
Figure 5B:
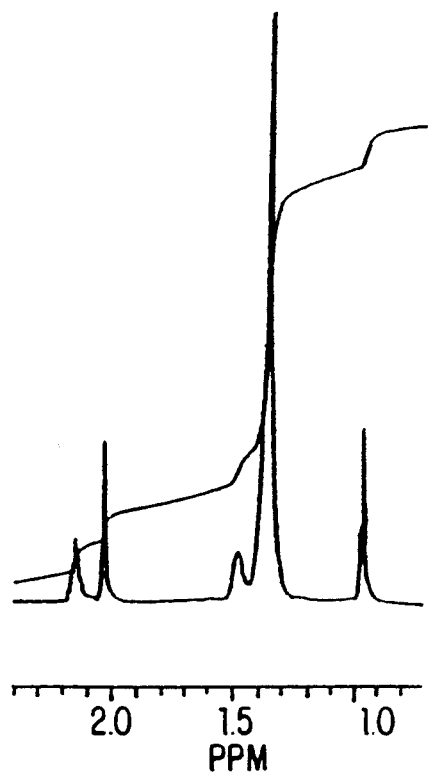
Figure 5C:
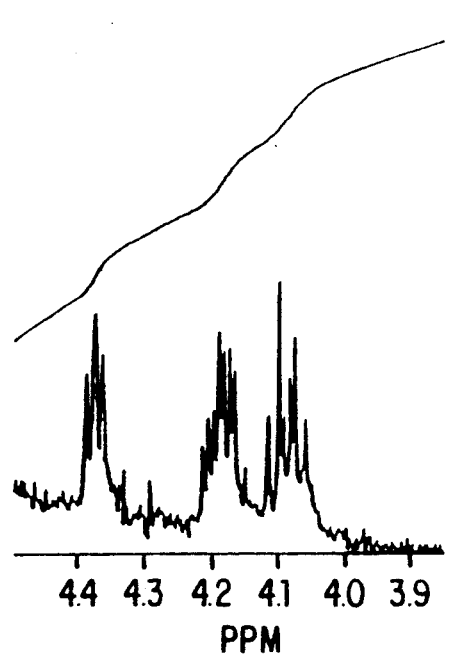
Figure 5D:
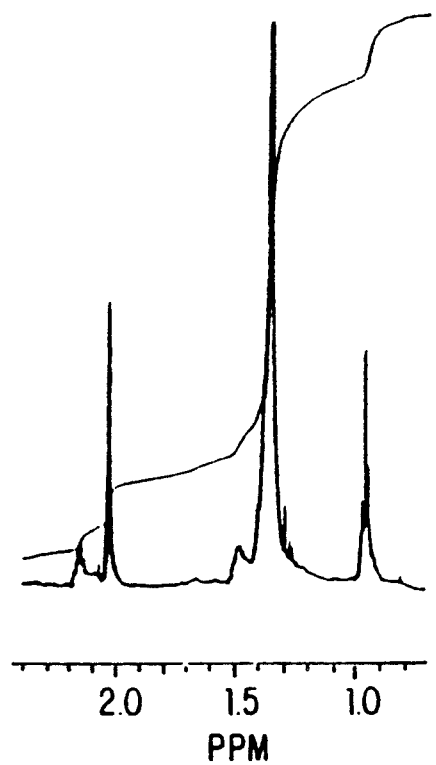

FIGS. 5A-D, are portions of the $^1H$-NMR spectra (500 MHz) of SPN-1-P made from sphingosylphosphocholine with phospholipase D (FIGS. 5A and 5B) and of SPN-1-P chemically synthesized (FIGS. 5C and 5D). The spectra were taken in methyl-$^{12}C$-$d_3$-alcohol-d-acetic-$d_3$-acid-d 8:2 (v/v).

The small difference in NMR spectrum reflects the fact that enzymatically-synthesized SPN-1-P contains a small amount of L-threo isomer, whereas chemically-synthesized SPN-1-P does not contain any detectable amount of L-threo isomer.

EXAMPLE II

ASSAYS FOR CHEMOTACTIC CELL MOTILITY AND CHEMOINVASION USING TRANSWELL PLATES

Assays were performed using transwell plates with polycarbonate membrane filters (pore size 8 µm) (Costar Scientific, Cambridge, Mass.). 50 µl aliquots of an aqueous solution of MATRI-GEL (Collaborative Research, Bedford, Mass.) containing 20 µg/ml (for chemotactic motility assay) or 200 µg/ml (for chemoinvasion assay) were added to each well and dried overnight. The filter was fitted onto the lower chamber plate. The lower chamber contained 0.6 ml conditioned medium (CM) (i.e., medium used for splenic stromal cell culture, and containing motility factor secreted by these cells) with or without the suspected inhibitor. To the upper chamber was added 100 µl of cell suspension ($5 \times 10^4$ cells/ml for invasion assay, $5 \times 10^5$ cells/ml for motility assay), which was then incubated in 5% $CO_2$ at 37° C. for 70-72 hours (invasion assay) or 20 hours (motility assay). After incubation, cells remaining in the upper chamber were wiped off with a cotton swab, and cells which had migrated to the lower chamber side of the filter were fixed in methanol for 30 seconds and stained with 0.05% toluidine blue. The filter was removed, the stain was solubilized in 10% acetic acid (0.1 ml for invasion assay, 0.5 ml for motility assay), and color intensity (optical density) was quantitated by ELISA reading at 630 nm. A schematic summary of this procedure is shown in FIG. 6. A linear relationship was observed between cell number and toluidine blue optical density (FIG. 7.).

Inhibition of Chemotactic Cell Motility by SPN-1-P

Figure 8:
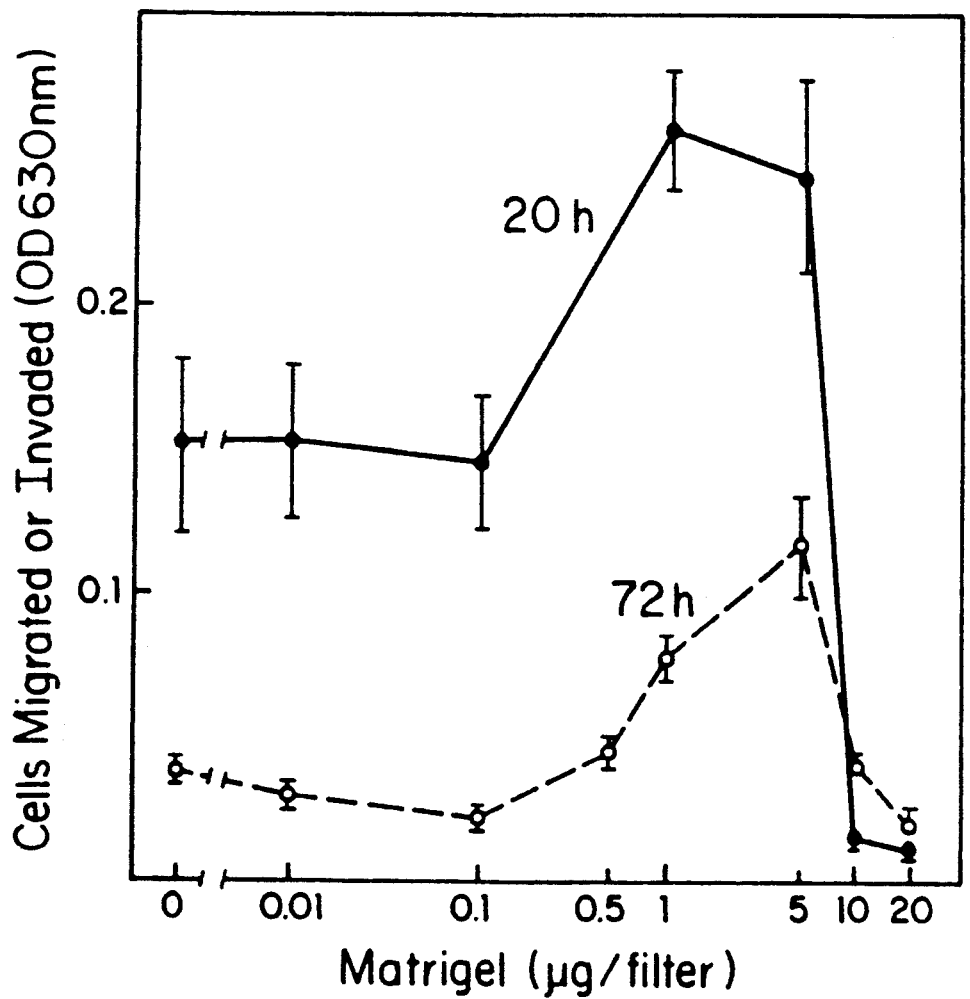
FIG. 8 is a graph depicting data that demonstrates the rationale for selection of MATRI-GEL quantity coated on transwell polycarbonate membrane. The ordinate represents the number of migrating cells (determined by toluidine blue absorbance), and the abscissa represents the quantity of MATRI-GEL applied. Closed circles represent migration determined after 20 hours, and open circles represent migration determined after 72 hours. For 20 hour duration, maximal migration was observed when 1 μg MATRI-GEL was coated per well filter, so this quantity was used for the chemotactic motility assay. For the 72 hour duration, no migration was observed when 20 μg MATRI-GEL per well was applied, but some migration occurred with 10 μg per well. Therefore, 10 μg was used for the chemoinvasion assay.

In experiments with different quantities of MATRI-GEL, cell migration through transwell filter was maximal with 1 µg/well was applied, and when CM was used (FIG. 8). Therefore, chemotactic cell motility, as affected by various SPN derivatives, was assayed under these conditions.

Figure 9:
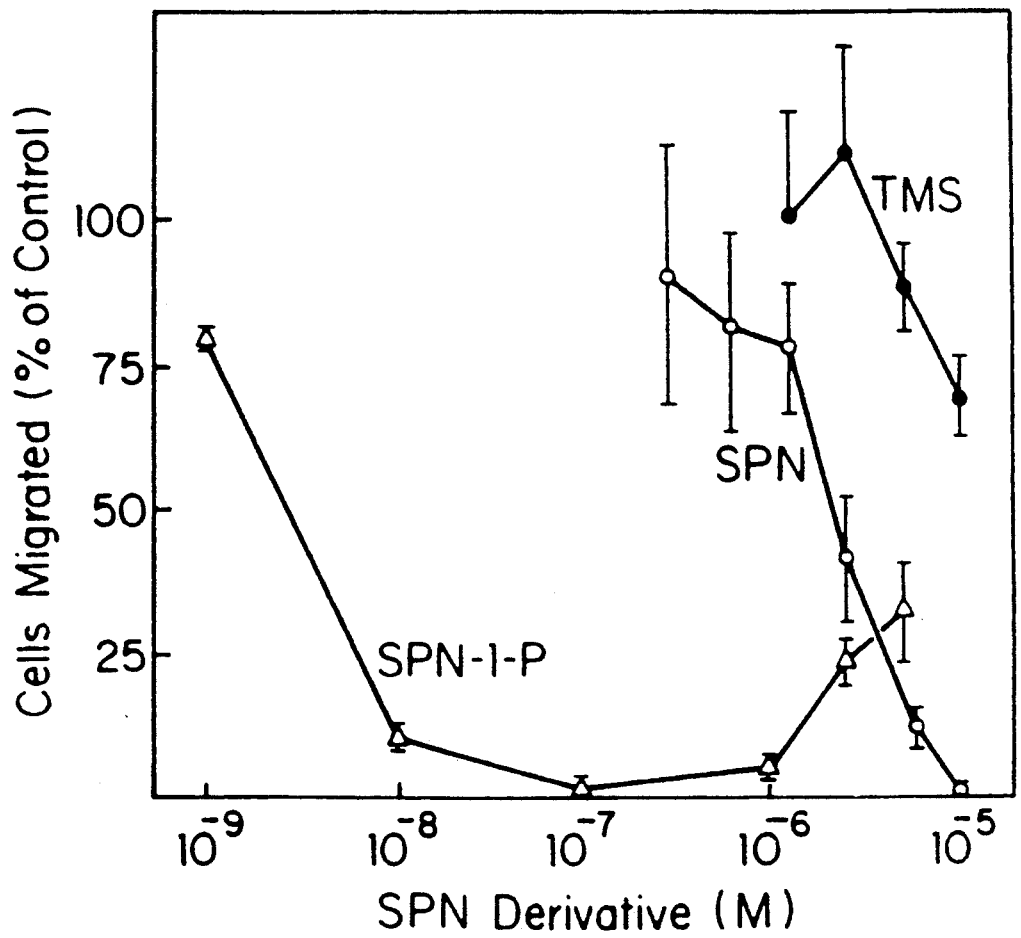
FIG. 9 is a graph showing chemotactic motility of mouse B16/F1 cells through a polycarbonate transwell membrane coated with 1 μg/well MATRI-GEL after 20 hour incubation. The ordinate represents the percent of cell number migrated relative to control. The abscissa represents concentration of SPN or SPN-derivative in conditioned medium (CM) added to the lower chamber. SPN-1-P represents sphingosine-1-phosphate and TMS represents N,N,N-trimethylsphingosine.

The results for chemotactic motility of mouse melanoma B16/F1 cells are shown in FIG. 9. In FIG. 9, the ordinate represents the percent of cell number migrated relative to control, and the abscissa represents concentration of SPN or SPN-derivative in CM added to the lower chamber. The results establish that the motility for mouse melanoma B16/F1 cells was inhibited most strongly by SPN-1-P, followed by SPN and TMS. Motility (i.e., penetration through the MATRI-GEL-coated filter) was 100% blocked by $10^{-7}$M SPN-1-P, and 90% blocked by $10^{-8}$M SPN-1-P. Both enzymatically- and chemically-synthesized SPN-1-P showed the same dose-dependent inhibitory effect on cell motility. A much higher concentration ($10^{-5}$M) of SPN was required for 100% blocking. $10^{-5}$M TMS produced only weak inhibition of motility. The higher effectiveness of SPN compared to TMS is due to the fact that SPN can be converted to SPN-1-P, whereas TMS cannot be phosphorylated.

Inhibition of Chemoinvasion

Chemoinvasion was measured by the ability of tumor Cells in CM (as described above) to migrate through a thick layer of MATRI-GEL during a prolonged incubation period (70 hours). This property is distinct from chemotactic cell motility, which involves a much shorter incubation period (20 hours) and a thin layer of MATRI-GEL. For the chemoinvasion assay, 10 μg of MATRI-GEL was applied to a polycarbonate transwell filter and migration was observed following 70 hours incubation (based on results shown in FIG. 8).

Figure 10:
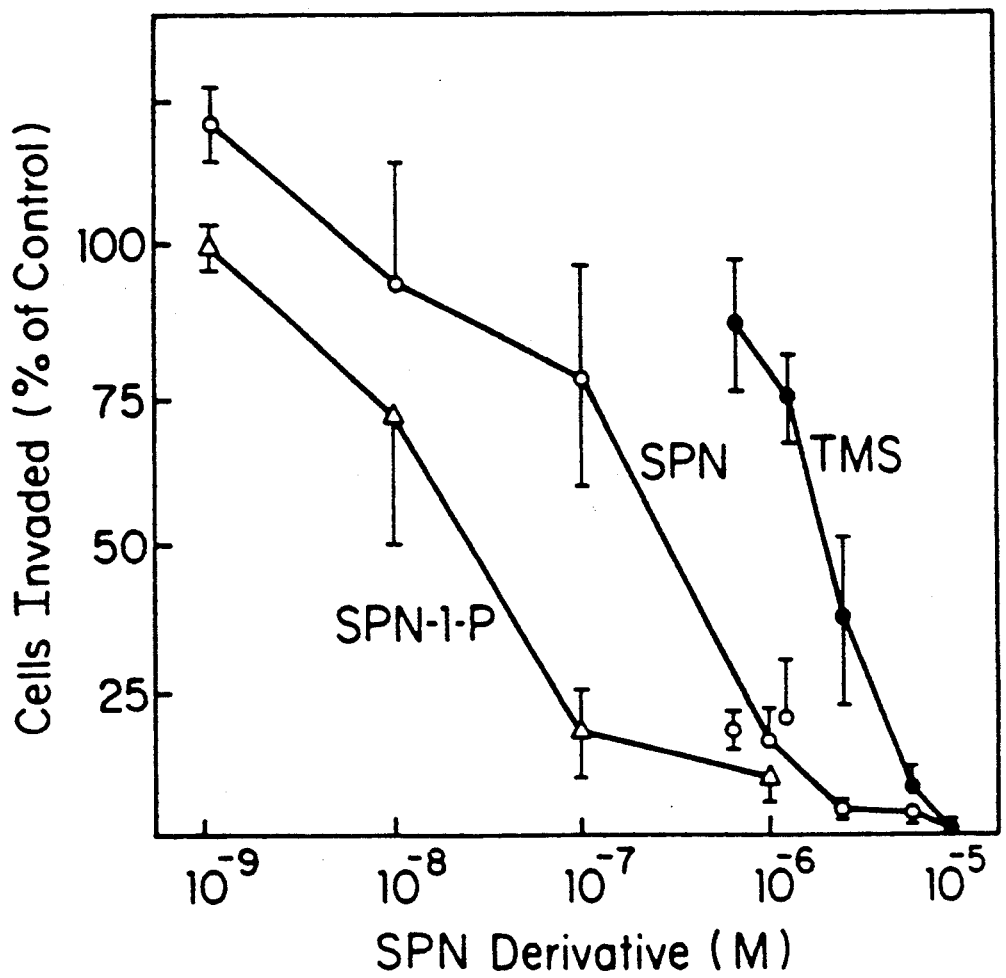
FIG. 10 is a graph showing chemoinvasion of B16/F1 cells through a polycarbonate transwell membrane coated with 10 μg/well MATRI-GEL after 70 hours incubation. The ordinate, abscissa and abbreviations are the same as described for FIG. 9.

The results are shown in FIG. 10. In FIG. 10, the ordinate represents the percent of cell number migrated relative to control, and the abscissa represents the concentration of SPN or SPN-derivative (in CM) added to the lower chamber. The results show that under these conditions, invasion of B16/F1 cells was strongly inhibited by $10^{-8}$ or $10^{-7}$M SPN-1-P, whereas SPN and TMS had a weaker effect. The difference in effect for SPN-1-P vs. SPN or TMS was not as pronounced as for motility.

Comparative effects of various sphingolipids on chemotactic cell motility and chemoinvasion of B16/F1 cells are summarized in Table IV. Effect of SPN-1-P on motility of various cells is shown in Table V. Susceptibility of B16/F1 and B16/F10 cells to SPN-1-P was high, whereas that of human fibrosarcoma HT1080 cells was low.

TABLE IV

Comparative effects of sphingolipids on chemotactic motility and chemoinvasion of B16/F1 melanoma cells.

| Sphingolipid | % motility | % invasion |
|---|---|---|
| control | 100 ± 9 | 100 ± 20 |
| SPN | 78 ± 11* | 16 ± 7 |
| SPN-1-P | 5 ± 1 | 12 ± 4 |
| phosphoethanolamine | 86 ± 20 | 160 ± 57 |
| ethanolamine | 85 ± 13 | 140 ± 41 |
| phosphatidylethanolamine | 107 ± 18 | 104 ± 37 |
| Cer (Sigma, type III) | 101 ± 26 | |
| 8-Cer | 125 ± 15 | 82 ± 13 |
| N-acetyl-SPN | 99 ± 16 | 96 ± 14 |
| CMH | 162 ± 29 | 178 ± 70 |
| GM3 | 140 ± 26 | 127 ± 69 |
| sphingomyelin | 82 ± 11 | 138 ± 18 |
| sulf-SPN | 114 ± 36 | 160 ± 23 |
| Cer-1-P | 136 ± 12 | 37 ± 18 |
| TMS | 100 ± 19 | 75 ± 8 |

*Mean ± S.E. of percent relative to control (n = 3 or 4).

TABLE V

Effect of SPN-1-P on chemotactic motility through MATRI-GEL-coated polycarbonate filter of mouse melanoma B16/F1 and B16/F10 cells, mouse Balb/c 3T3 fibroblasts, and human fibrosarcoma HT1080 cells.

| SPN-1-P dose (μM) | Relative Motility | | | |
|---|---|---|---|---|
| | F1 | F10 | 3T3 | HT1080 |
| 5.0 | — | — | 11 ± 1 | 64 ± 4 |
| 1.0 | 8 ± 2* | 4 ± 1 | 40 ± 1 | 105 ± 14 |
| 0.1 | 6 ± 2 | 4 ± 2 | 101 ± 10 | 115 ± 35 |
| 0.01 | 12 ± 7 | 10 ± 4 | 125 ± 5 | 100 ± 30 |
| 0.001 | 82 ± 44 | 96 ± 21 | 119 ± 9 | 100 ± 21 |
| control | 100 ± 9 | 100 ± 16 | 100 ± 10 | 100 ± 10 |

*Mean ± S.E. of percent relative to control (n = 4). Actual O.D. values of controls (defined as 100%) were 0.114 (F1), 0.199 (F10), 0322 (3T3), and 0.147 (HT1080). 6 × $10^4$ cells were placed on a transwell filter coated with 1.0 μg MATRI-GEL in the upper chamber, and cultured for 18 hours in the presence of CM and SPN-1-P in the lower chamber.

EXAMPLE III

PHAGOKINETIC ASSAY USING GOLD SOL-COATED PLATES

Cell motility was estimated as the area of phagokinetic track on gold sol particle-coated plates as previously described {Albrecht-Buehler, Cell, 11:395 (1977)}. A uniform coating of gold particles was prepared on glass coverslips precoated with bovine serum albumin, and the coverslips were rinsed repeatedly to remove non-adhering or loosely-adhering gold particles. Freshly-prepared neutrophils or tumor cells detached from culture were placed in a Petri dish containing the gold sol-coated plate, and incubated for 2 hours (for human neutrophils) or 18 hours (for tumor cells). The coverslips were fixed for 1 hour in 4% formaldehyde solution in phosphate-buffered saline (PBS) and mounted on microscope slides. The phagokinetic tracks were observed on a television connected to a light microscope (Nikon, Tokyo, Japan). Tracks on the television were transferred to translucent sheets, which were then photocopied. Phagokinetic activity was quantitated by cutting and weighing the swept area in the copy.

Figure 1:
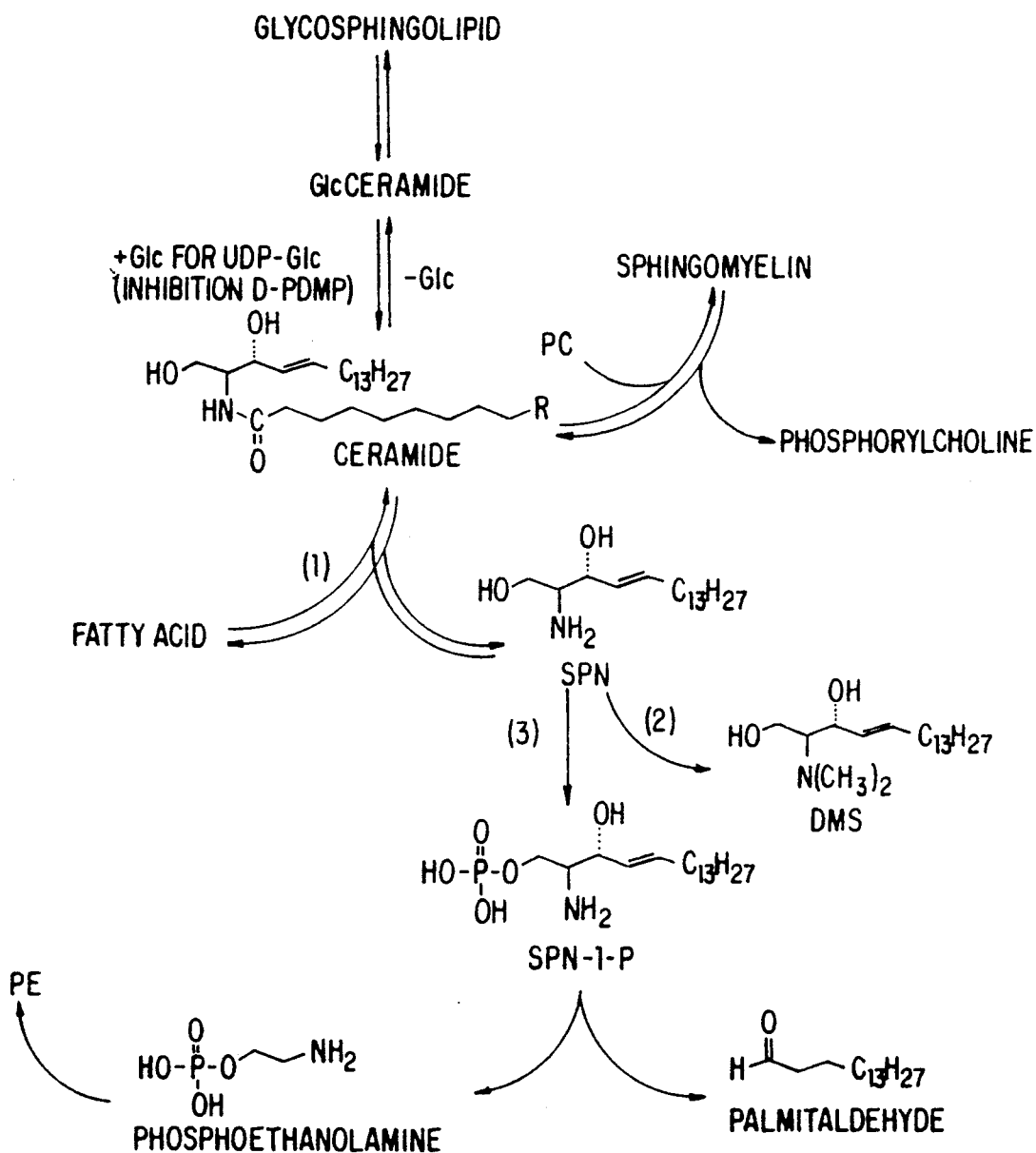
FIG. 1 depicts the metabolic relationships in synthesis and degradation of sphingolipids. All glycosphingolipids (except GalCer and its derivatives) are synthesized through GlcCer, which is synthesized from ceramide (Cer) through UDP-Glc. Cer is degraded into fatty acids and SPN (route 1). SPN is degraded through phosphorylation into SPN-1-P through SPN kinase (route 2), which is in turn degraded into phosphoethanolamine and s palmital. SPN can also be converted into dimethylsphingosine (DMS) by transmethylation (route 3). Cer is converted to sphingomyelin by transfer of phosphorylcholine from phosphatidylcholine.
Figure 2:
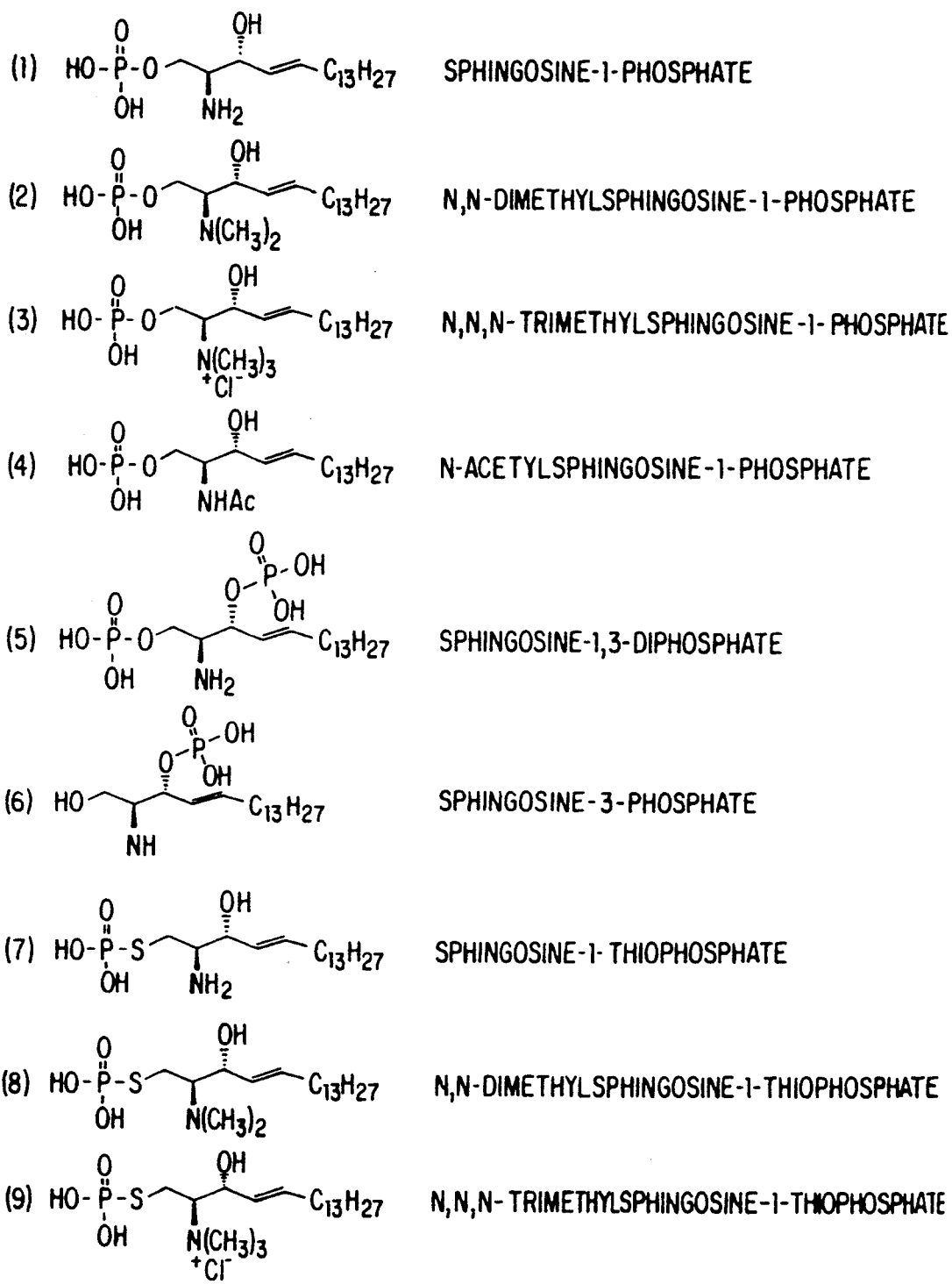
FIG. 2 gives the structure of SPN-1-P and various synthetic derivatives of SPN-1-P.

The results for inhibition of phagokinetic activity of tumor cells by SPN-1-P are shown in FIGS. 11A-F. FIGS. 11A-F show the gold sol clearance patterns of B16/F1 cells. FIG. 11A: control cells in CM without SPN-1-P; FIG. 11B: CM plus 1.0 μM SPN-1-P; FIG. 11C: CM plus 0.1 μM SPN-1-P; FIGS. 11D-F show areas cleared in the absence of or in the presence of various concentrations of SPN-1-P: FIG. 11D, 0 μM SPN-1-P; FIG. 11E, 0.1 μM SPN-1-P; FIG. 11F, 1.0 μM SPN-1-P.

The results show that addition of SPN or its derivatives to the culture medium reduced the area cleared by tumor cells. In particular, average cleared area was greatly reduced when SPN-1-P was added at a concentration of 1.0 or even 0.1 μM. The comparative effects of various SPN derivatives on B16/F10 phagokinetic activity are summarized in Table VI.

TABLE VI

Effect of SPN, SPN-1-P, and TMS on phagokinetic activity of B16/F10 melanoma cells.

| | | Cleared area (× $10^3$ μm$^2$) | |
|---|---|---|---|
| Compound | Conc. (μM) | less control (CM−) value | % of control (CM+) value |
| Control (CM−) | | 2.1 ± 0.9* | 0 |
| Control (CM+) | | 6.9 ± 3.4 | 4.8 | 100 |

TABLE VI-continued

Effect of SPN, SPN-1-P, and TMS on phagokinetic activity of B16/F10 melanoma cells.

| Compound | Conc. (μM) | Cleared area ($\times 10^3$ μm$^2$) less control (CM−) value | % of control (CM+) value |
|---|---|---|---|
| SPN | 1.0 | 2.5 ± 1.0$^a$ | 0.4 | 8 |
| SPN-1-P | 1.0 | 2.4 ± 1.1$^a$ | 0.3 | 6 |
|  | 0.1 | 3.4 ± 1.3$^a$ | 1.3 | 27 |
|  | 0.01 | 4.1 ± 1.4$^a$ | 2.0 | 42 |
|  | 0.0001 | 6.0 ± 2.7 | 3.9 | 81 |
| TMS | 1.0 | 5.6 ± 2.7$^b$ | 3.5 | 73 |

*Mean ± S.D. (n > 50). $10^3$ B16/F10 cells were seeded on a coverslip precoated with gold sol particles in the presence or absence of SPN derivative. 18 hours later, the cleared area was estimated as described in the text. $^a$p < 0.0001, $^b$p < 0.05 compared to control. Using B16/F1 cells, similar results were obtained (data not shown).

The effects of SPN derivatives on myeloid cell phagokinesis are shown in Table VII. As seen from the data in Table VII, reduction of phagokinetic activity of human neutrophils was most striking for SPN-1-P and TMS.

TABLE VII

Effect of SPN, SPN-1-P, and TMS on phagokinetic activity of human neutrophils.

| Compound | Conc. (μM) | n* | Cleared area ($\times 10^3$ μm$^2$) |
|---|---|---|---|
| Control |  | 141 | 6.3 ± 2.3** |
| SPN | 0.45 | 81 | 5.2 ± 2.0$^a$ |
| TMS | 0.45 | 94 | 5.4 ± 2.7$^c$ |
|  | 1.0 | 100 | 3.6 ± 1.5$^a$ |
| SPN-1-P | 0.45 | 80 | 5.5 ± 2.7$^c$ |
|  | 1.0 | 74 | 5.4 ± 2.4$^b$ |
|  | 4.5 | 123 | 3.5 ± 1.4$^a$ |
| phospho-ethanolamine | 4.5 | 70 | 5.9 ± 2.5 |
| Cer | 4.5 | 75 | 5.7 ± 3.0 |

* n, number of neutrophils examined.
** mean ± S.D. Freshly-prepared neutrophils (1 × $10^4$ cell/plate) were seeded on a coverslip precoated with gold sol particles in the presence or absence of test compound. 2 hours later, incubation was terminated by adding 200 μl of 10% formaldehyde and the cleared area was estimated as described in the text. $^a$p < 0.001, $^b$p < 0.025, $^c$p < 0.05 compared to control.

While the invention has been described in detail above with reference to a preferred embodiment, various modifications within the scope and spirit of the invention will be apparent to people of working skill in this technological field.

What is claimed:

1. A method of inhibiting tumor cell chemotactic motility comprising contacting said tumor cells with an inhibitory amount of sphingosine-1-phosphate or a derivative of sphingosine-1-phosphate, wherein said derivative of sphingosine-1-phosphate is selected from the group consisting of N,N-dimethylsphingosine-1-phosphate, N,N,N,-trimethylsphingosine-1-phosphate, N-acylsphingosine-1-phosphate, sphingosine-1,3-diphosphate, sphingosine-3-phosphate, sphingosine-1-thiophosphate, N,N-dimethylsphingosine-1-thiophosphate, N-acylsphingosine-1-thiophosphate and N,N,N-trimethylsphingosine-1-thiophosphate.

2. The method of claim 1, wherein sphingosine-1-phosphate is used.

3. The method of claim 1, wherein said N-acylsphingosine is N-acetylsphingosine.

4. A method of inhibiting tumor cell chemoinvasion comprising contacting said tumor cells with an inhibitory amount of sphingosine-1-phosphate or a derivative of sphingosine-1-phosphate, wherein said derivative of sphingosine-1-phosphate is selected from the group consisting of N,N-dimethylsphingosine-1-phosphate, N,N,N,-trimethylsphingosine-1-phosphate, N-acylsphingosine-1-phosphate, sphingosine-1,3-diphosphate, sphingosine-3-phosphate, sphingosine-1-thiophosphate, N,N-dimethylsphingosine-1-thiophosphate, N-acylsphingosine-1-thiophosphate and N,N,N-trimethylsphingosine-1-thiophosphate.

5. The method of claim 4, wherein sphingosine-1-phosphate is used.

6. The method of claim 4, wherein said N-acylsphingosine is N-acetylsphingosine.

7. A method of inhibiting phagokinetic activity of tumor cells and neutrophils comprising contacting said cells with a phagokinetic inhibitory amount of sphingosine-1-phosphate or a derivative of sphingosine-1-phosphate, wherein said derivative of sphingosine-1-phosphate is selected from the group consisting of N,N-dimethylsphingosine-1-phosphate, N,N,N,-trimethylsphingosine-1-phosphate, N-acylsphingosine-1-phosphate, sphingosine-1,3-diphosphate, sphingosine-3-phosphate, sphingosine-1-thiophosphate, N,N-dimethylsphingosine-1-thiophosphate, N-acylsphingosine-1-thiophosphate and N,N,N-trimethylsphingosine-1-thiophosphate.

8. The method of claim 7, wherein sphingosine-1-phosphate is used.

9. The method of claim 7, wherein said N-acylsphingosine is N-acetylsphingosine.

10. A method of inhibiting tumor cell metastasis comprising administering to a host in need of treatment a metastasis inhibitory amount of an agent selected from the group consisting of sphingosine-1-phosphate and a derivative of sphingosine-1-phosphate, and pharmaceutically acceptable salts of said agent, wherein said derivative of sphingosine-1-phosphate is selected from the group consisting of N,N-dimethylsphingosine-1-phosphate, N,N,N,-trimethylsphingosine-1-phosphate, N-acylsphingosine-1-phosphate, sphingosine-1,3-diphosphate, sphingosine-3-phosphate, sphingosine-1-thiophosphate, N,N-dimethylsphingosine-1-thiophosphate, N-acylsphingosine-1-thiophosphate and N,N,N-trimethylsphingosine-1-thiophosphate.

11. The method of claim 10, wherein sphingosine-1-phosphate is used.

12. The method of claim 10, wherein said N-acylsphingosine is N-acetylsphingosine.

* * * * *

UNITED STATES PATENT AND TRADEMARK OFFICE
CERTIFICATE OF CORRECTION

PATENT NO. : 5,260,288

DATED : November 9, 1993

INVENTOR(S) : Yasuyuki Igarashi et al.

It is certified that error appears in the above-indentified patent and that said Letters Patent is hereby corrected as shown below: On the title page, item [75]:

Inventors line 1, change "Fugiang to -- Fuqiang --;

Column 1, line 24, change "pyridoxa" to -- pyridoxal --;
         line 30, change "BioI." to -- Biol. --; and
         line 51, change "streptomuces" to -- Streptomyces --.

Column 2, line 58, change "s palmital" to -- palmital --; and
         64, change "3C" to -- 3I --.

Column 6, line 35, change "PKS" to -- PKC --.

Column 8, line 25, change "arr" to -- art --;
         line 34, change "6" to -- 6th --; and
         line 38, change "disfunction" to -- dysfunction --.

Column 9, line 27, change "(Compound" to -- (Compound I). --; and
         line 45, change "precting" to -- protecting --.

Column 13, line 21, change "Cells" to -- cells --.

Column 14, line 15, change "0322" to -- 0.322 --; and
          line 57, change "greatlY" to -- greatly --.

Signed and Sealed this

First Day of November, 1994

Attest:

BRUCE LEHMAN

*Attesting Officer*  *Commissioner of Patents and Trademarks*